(12) United States Patent
Feng et al.

(10) Patent No.: US 9,925,171 B2
(45) Date of Patent: Mar. 27, 2018

(54) COMPOUND HAVING HIGHER INHIBITORY ACTIVITY ON PROTEIN KINASE G AND PREPARATION METHOD THEREOF

(71) Applicant: Jenkem Technology Co., Ltd. (Tianjin), Tianjin (CN)

(72) Inventors: Zewang Feng, Tianjin (CN); Xuan Zhao, Tianjin (CN); Zhenguo Wang, Tianjin (CN); Yan Liu, Tianjin (CN)

(73) Assignee: JENKEM TECHNOLOGY CO., LTD., (TIANJIN), Tianjin (CN)

(*) Notice: Subject to any disclaimer, the term of this patent is extended or adjusted under 35 U.S.C. 154(b) by 0 days.

(21) Appl. No.: 15/409,403

(22) Filed: Jan. 18, 2017

(65) Prior Publication Data

US 2017/0119736 A1 May 4, 2017

Related U.S. Application Data

(60) Division of application No. 15/146,588, filed on May 4, 2016, now Pat. No. 9,567,319, which is a continuation of application No. PCT/CN2014/090226, filed on Nov. 4, 2014.

(30) Foreign Application Priority Data

Nov. 4, 2013 (CN) .......................... 2013 1 0540726

(51) Int. Cl.

| | | |
|---|---|---|
| A61K 31/40 | (2006.01) | |
| A61K 31/416 | (2006.01) | |
| C07C 69/76 | (2006.01) | |
| C07C 65/40 | (2006.01) | |
| C07D 207/16 | (2006.01) | |

(52) U.S. Cl.
CPC ............ *A61K 31/416* (2013.01); *C07C 65/40* (2013.01); *C07C 69/76* (2013.01); *C07D 207/16* (2013.01)

(58) Field of Classification Search
CPC ..... C07D 403/12; A61K 31/40; A61K 31/416
See application file for complete search history.

(56) References Cited

U.S. PATENT DOCUMENTS

| | | |
|---|---|---|
| 6,476,007 B2 | 11/2002 | Tao et al. |
| 8,846,742 B2 | 9/2014 | Ambron et al. |
| 9,567,319 B2 | 2/2017 | Feng et al. |
| 2008/0176920 A1 | 7/2008 | Ambron et al. |
| 2016/0304501 A1 | 10/2016 | Feng et al. |

FOREIGN PATENT DOCUMENTS

| | | |
|---|---|---|
| CN | 1283643 A | 2/2001 |
| WO | WO-2006/102267 A2 | 9/2006 |
| WO | WO-2006/102267 A3 | 9/2006 |
| WO | WO-2007/095586 A2 | 8/2007 |
| WO | WO-2007/095586 A3 | 8/2007 |

OTHER PUBLICATIONS

Written Opinion dated Feb. 6, 2015 for PCT Application No. PCT/CN2014/090226, filed Nov. 4, 2014, 4 pages.
Written Opinion dated Feb. 6, 2015 for PCT Application No. PCT/CN2014/090226, filed Nov. 4, 2014, 6 pages. (English translation).
Bruckdorfer, T. et al. (2009). "Pegylation- A Key Technology to improve Solubility and Pharmacokinetic of Peptides, Proteins and Other Biopharmaceuticals for Superior Drug Delivery," 21st American Peptide Symposium, Bloomington, IN, USA Jun. 7-12, 2009, *Poster Session I Abstracts*P137.
Extended European Search Report dated Apr. 7, 2017, for EP Application No. 14857892.5, 8 pages.
Li, D. et al. (Oct. 5, 2013). "A novel chlorin-PEG-folate conjugate with higher water solubility, lower cytotoxicity, better tumor targeting and photodynamic activity," *Journal of Photochemistry and Photobiology B: Biology*128:28-37.
Mahendran, A. et al. (Aug. 16, 2010). "Synthesis, characterization, mechanism of decomposition, and antiproliferative activity of a class of PEGylated benzopolysulfanes structurally similar to the natural product varacin," *Journal of Organic Chemistry*75(16). 5549-5557.
Shen, J. et al. (Nov. 1, 2013, e-published Aug. 21, 2013). "Synthesis, characterization, in vitro and in vivo evaluation of PEGylated oridonin conjugates," *International Journal of Pharmaceutics*456(1):80-86.

*Primary Examiner* — Sudhakar Katakam
(74) *Attorney, Agent, or Firm* — Mintz, Levin, Cohn, Ferris, Glovsky and Popeo, P.C.

(57) ABSTRACT

Disclosed are a compound of Formula I,

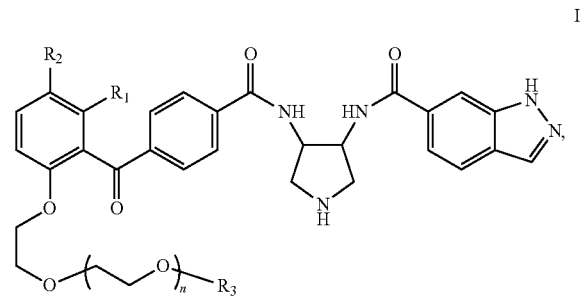

having higher inhibition of protein kinase G (PKG) activity and pharmaceutically acceptable salts thereof. In Formula I, $R_1$ and $R_2$ are the same or different, each being independently chosen from the halogens, the $C_1$-$C_6$ alkoxyl group, the $C_1$-$C_6$ alkyl group, the $C_2$-$C_6$ alkenyl group, and the $C_2$-$C_6$ alkynyl group; $R_3$ is chosen from H, the halogens, the substituted or unsubstituted $C_1$-$C_6$ alkyl group, $C_3$-$C_6$ cycloalkyl group, $C_2$-$C_6$ alkenyl group, and $C_2$-$C_6$ alkynyl group, aryl group, and heteroaryl group; and n is an integer between 0 and 15. Also disclosed is a pharmaceutical composition comprising said compound, the use of the compound in treating pains, in particular chronic pain, a preparation method for the compound, and a new intermediate.

13 Claims, 6 Drawing Sheets

COMPOUND HAVING HIGHER INHIBITORY ACTIVITY ON PROTEIN KINASE G AND PREPARATION METHOD THEREOF

CROSS-REFERENCES TO RELATED APPLICATIONS

This application is a divisional of U.S. application Ser. No. 15/146,588, filed May 4, 2016, now U.S. Pat. No. 9,567,319, which is a continuation of International Appl. No. PCT/CN2014/090226, filed Nov. 4, 2014, which claims the benefit of Chinese Patent Appl. No. 201310540726.X 2013, filed Nov. 4, 2013, each of which is incorporated herein by reference in its entirety and for all purposes.

BACKGROUND OF THE INVENTION

The present invention relates to a class of novel compounds, to methods and intermediates for preparing the compounds, to pharmaceutical compositions comprising the compounds, and to use of the compounds and the pharmaceutical compositions. Specifically, the present invention relates to a class of compounds having higher inhibitory activity on protein kinase G (PKG), to methods and intermediates for preparing the compounds, to pharmaceutical composition comprising the compounds, and to use of the compounds and the pharmaceutical compositions for treating pain, especially for treating chronic pain.

Pain is a result of communication between two major nervous systems, i.e., the central and peripheral nervous systems. Subjective experiences of humans are resulted from the combined effects of the two major nervous systems, which, however, are different in physiological structure and function.

The pain stimulation resulted from the impact on a particular pain receptor transmits along the primary nociceptive sensory neurons at a dorsal root ganglion (DRG, a part of the peripheral nervous system), and then transmits in the spinal cord (a part of the central nervous system), where the signal is forwarded to the second-order neurons, transmitted to the opposite side of the spinal cord, and finally transmitted to a higher center in brain, where pain is sensed.

The peripheral pain receptors having response to mechanical, heat and chemical stimulations are positioned at the nerve endings of the primary nociceptive sensory neurons. The activation of these receptors can result in acute or chronic pain. The acute pain tends to be intense and indiffusible, and generally transmits along the axon having a thin myelin sheath of a delta sensory neuron. The chronic pain tends to be dull and diffusible, and generally transmits along the unmyelinated axon of a C-type nociceptive sensory neuron.

At different stages of a pain pathway, the pain perception may be changed. For example, the pain stimulation can be eliminated when a local anesthetic is administered to a peripheral receptor. As is known to all, in the pain pathway, drugs like paperamine exhibit an inhibitory effect in the central nervous system, and non-steroidal anti-inflammatory drugs exhibit an inhibitory effect in the peripheral nervous system. Generally, the chronic pain perception in a non-primary spinal cord injury is not only related to the sensitization of the peripheral pain receptor, but also related to the alteration of the excitability of the second-order neuron. There are peripheral and central nervous systems, which adjust "primary" and "secondary" hyperalgesias, respectively. In the secondary hyperalgesia, the gene expression of the second-order neuron in the central nervous system alters, which results in the phenomenon of "central sensitization" or "spinal cord hyperalgesia". The N-methyl-D-aspartic acid (NMDA) receptor in the spinal cord plays an important role in this process. A spinal cord injury without the activation of the peripheral nervous system can also result in spinal cord hyperalgesia, causing central pain syndrome. Central neuropathic pain is related to the phosphorylation of cAMP response element-binding protein (CREB) transcriptional factor.

Chronic pain starts from periphery, and is caused by a neural injury (neuropathic pain) or inflammation. The pain caused by both of the causes is the major clinical problem which hinders an effective treatment. In models of humans and mammals, the constant pain after a neural injury is related to the long-term hyperexcitation (LTH) of primary sensory neurons, the axons of which are positioned at the injured ganglions. The long-term hyperexcitation occurs due to the increasing sensitization to the cell bodies and axons of pain sensory neurons at an injured site by electric stimulations. These alterations result in the release of action potential from sensory neurons at rest or without nociceptive stimulus, which causes a continuous excitation of high-order neurons in the central nervous system, spinal cord hyperalgesia and constant pain.

U.S. Pat. No. 6,476,007 relates to the mechanism of inflammatory hyperalgesia in the central nervous system, but the role of the peripheral nervous system is not considered therein. There are many significant disadvantages in drugs targeting the pain path of the central nervous system. Firstly, the neuronal circuits in the spinal cord are very complicated, and thus drugs predicted to relieve pain may have an opposite effect. Secondly, the blood-brain barrier, which separates the neurons in the central nervous system from the rest parts of the body, is generally a significant obstacle for a large number of therapeutic drugs to get to a target. Thirdly, drugs which cross the blood-brain barrier enter the entire central nervous system, causing significant toxic and side effects. Such an obstacle, however, does not exist in the peripheral nervous system. The structural characteristics of DRG show that treatment targeting a particular cluster of primary sensory neurons can be performed. Fourthly, pain can be perceived only when signals from the periphery are transmitted to the higher center in brain, and the neurons in DRG are the entrance for these signals.

Activated PKG plays a determinant role in the inhibition of pain (see WO2006/102267). After the peripheral nervous system is injured, the activity of nitric-oxide synthase (NOS) increases, which results in an improved yield of nitric oxide (NO). NO activates soluble guanylyl cyclase (sGC), and thus the level of cyclic guanosine monophosphate (cGMP) is raised, causing PKG activation in the axons of the C-type and A-δ-type pain neurons. Then, activated PKG transmits reversely along the axons from the injured site to the cell bodies of neurons, mitogen activated protein kinase-erk (MAPKerk). Subsequently, activated MAPKerk is transferred into nuclei, and adjusts the expression of pain related genes which adjust the presence of LTH. As such, the inhibition of PKG can relieve pain, and reduce the level of messenger RNA (mRNA) related to nociception proteins.

Therefore, compounds which can selectively inhibit the activity of PKG in the peripheral nervous system are needed in the art. The inhibition of activated PKG can not only prevent its transmission via the peripheral nervous system, but also block its activity in cells. US patent application No. US2008/0176920 describes compounds inhibiting the activated form of PKG, and use thereof in relieving pain, especially in relieving chronic pain syndrome. In this patent application, compound 46 is described as a compound having relatively higher activity. The inventors of the present application prepared compound 46 and its analog JK-02A according to the method described in US patent application No. US2008/0176920, and tested the activity of these agents. The test result shows that this class of compounds is not good enough in water solubility, and is not high enough in PKG inhibitory activity. As such, the inventors of the present application designed a class of compounds having better water solubility and higher inhibitory activity.

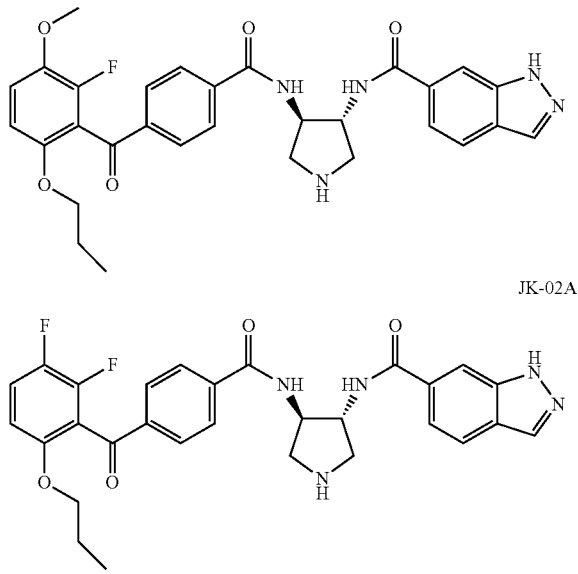

BRIEF SUMMARY OF THE INVENTION

In view that compound 46 designed in US patent application No. US2008/0176920 is not good enough in water solubility and PKG inhibitory activity, the inventors of the present invention made structural modifications to compound 46 by incorporating a low-molecular polyethylene glycol fragment with higher water solubility, so as to significantly improve the water solubility and the analgesic effect of the compound.

Accordingly, in one aspect, the present invention provides a compound of Formula I or a pharmaceutically acceptable salt thereof,

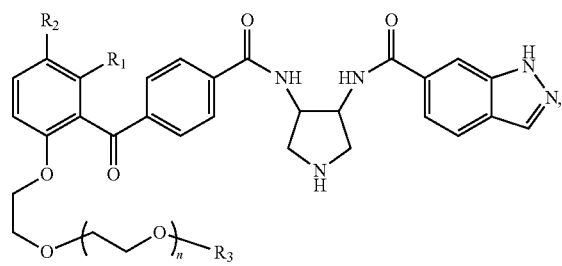

wherein $R_1$ and $R_2$ are the same or different, each independently selected from the group consisting of halogen, $C_1$-$C_6$ alkoxyl, $C_1$-$C_6$ alkyl, $C_2$-$C_6$ alkenyl and $C_2$-$C_6$ alkynyl; $R_3$ is selected from the group consisting of H, halogen, substituted or unsubstituted $C_1$-$C_6$ alkyl, $C_3$-$C_6$ cycloalkyl, $C_2$-$C_6$ alkenyl, $C_2$-$C_6$ alkynyl, aryl and heteroaryl; and n is an integer from 0 to 15.

The compound has higher water solubility and higher inhibitory activity on PKG, thereby providing a significantly improved analgesic effect.

In another aspect, the present invention provides use of the compound of Formula I or the pharmaceutically acceptable salt thereof in the manufacture of a medicament for treating pain.

In another aspect, the present invention provides a pharmaceutical composition comprising the compound of Formula I or the pharmaceutically acceptable salt thereof and one or more pharmaceutically acceptable carriers.

In another aspect, the present invention provides a method for treating pain, comprising administering to a subject in need thereof a therapeutically effective amount of the compound of the present invention or a pharmaceutically acceptable salt thereof, or the pharmaceutical composition of the present invention.

In yet another aspect, the present invention provides a method for preparing the compound of Formula I or the pharmaceutically acceptable salt thereof.

The above-described features and other features of the present invention will become more apparent from the following detailed description.

DETAILED DESCRIPTION OF THE INVENTION

Figure 1A:
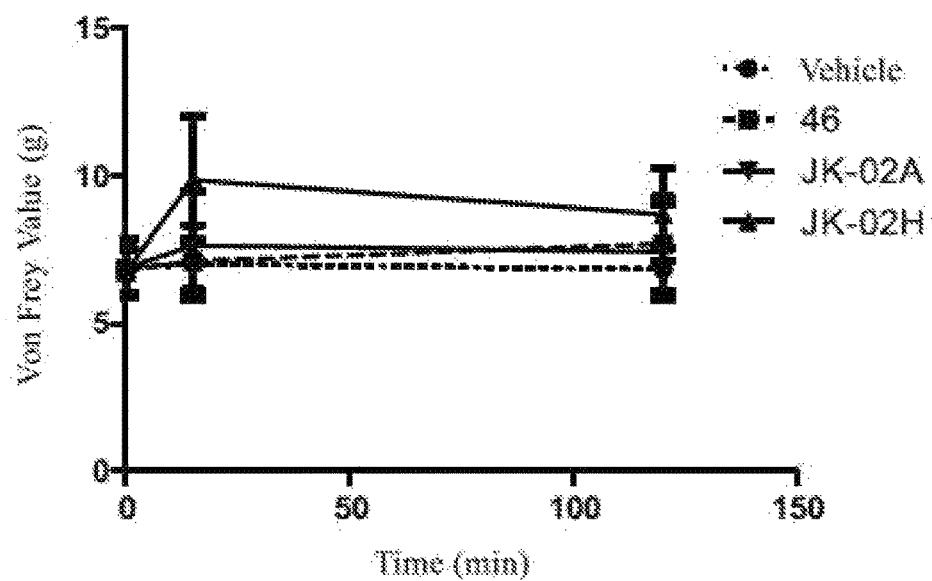
FIGS. 1A and 1B show the average value of each test compound in the Von Frey filament test under a low dose treatment.

The inventors of the present application discovered that compounds obtained by replacing the —$OCH_2CH_2CH_3$ group at position 6 of compound 46 disclosed in US2008/0176920 and a compound having a similar structure, JK-02A, with a low-molecular polyethylene glycol fragment have increased water solubility and exhibit higher inhibitory activity on PKG, indicating a significantly improved analgesic effect. The inventors of the present application also synthesized compounds having similar structures to the above-mentioned compounds, and investigation results showed that these compounds have significantly higher water solubility than their parent compounds, which would have a positive effect on the improvement of their pharmacological effect.

Accordingly, the present invention provides a compound of Formula I or a pharmaceutically acceptable salt thereof with higher PKG inhibitory activity for treating pain,

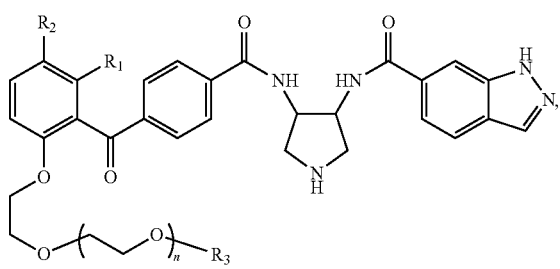

I wherein $R_1$ and $R_2$ are the same or different, each independently selected from the group consisting of halogen (such as F or Cl), $C_1$-$C_6$ alkoxyl, $C_1$-$C_6$ alkyl, $C_2$-$C_6$ alkenyl and $C_2$-$C_6$ alkynyl; $R_3$ is selected from the group consisting of H, halogen, substituted or unsubstituted $C_1$-$C_6$ alkyl, $C_3$-$C_6$ cycloalkyl, $C_2$-$C_6$ alkenyl, $C_2$-$C_6$ alkynyl, aryl and heteroaryl; and n is an integer from 0 to 15.

In a preferred embodiment of the present invention, $R_1$ and $R_2$ are each independently selected from the group consisting of halogen and $C_1$-$C_6$ alkoxyl. Preferably, $R_1$ is F, and $R_2$ is F or $OCH_3$.

In a preferred embodiment of the present invention, $R_3$ is selected from the group consisting of H and substituted or unsubstituted $C_1$-$C_6$ alkyl. More preferably, $R_3$ is selected from the group consisting of H and substituted or unsubstituted $C_1$-$C_3$ alkyl. Most preferably, $R_3$ is H, methyl or propyl.

In a preferred embodiment of the present invention, n is an integer from 0 to 10. More preferably, n is an integer from 1 to 6.

In a preferred embodiment of the present invention, $R_1$ is a fluorine atom, and $R_2$ is methoxyl. Accordingly, a preferred compound has a structure of Formula II:

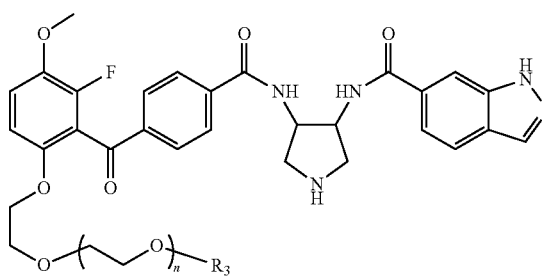

II wherein $R_3$ and n are as defined above.

In another preferred embodiment of the present invention, both $R_1$ and $R_2$ are fluorine atoms. Accordingly, a preferred compound has a structure of Formula III:

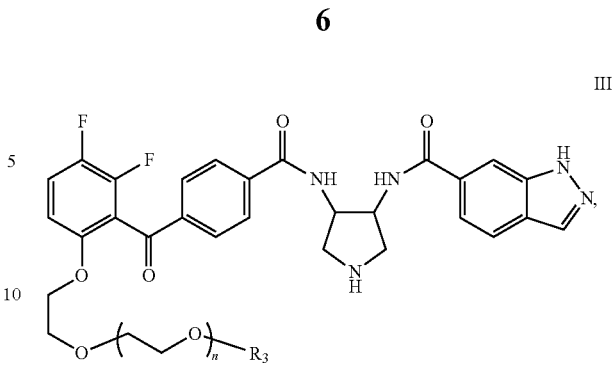

III wherein $R_3$ and n are as defined above.

Specifically, the present invention provides the following preferred compounds:

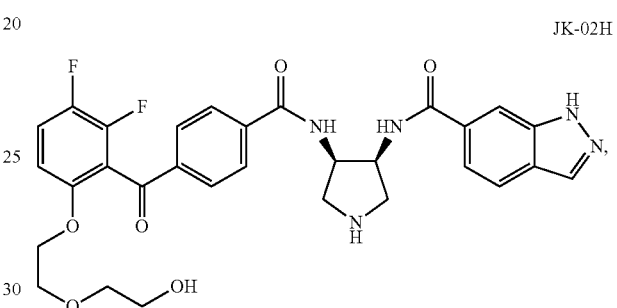

JK-02H

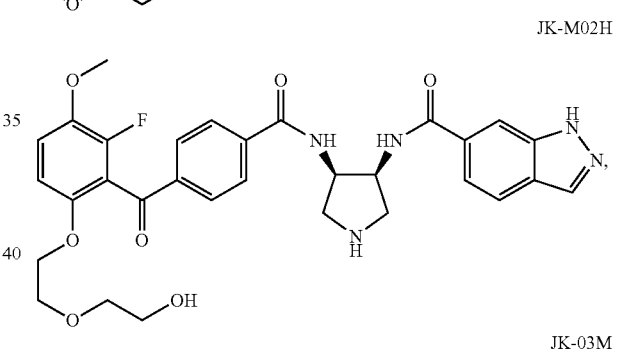

JK-M02H

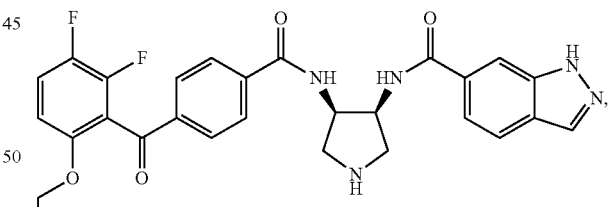

JK-03M

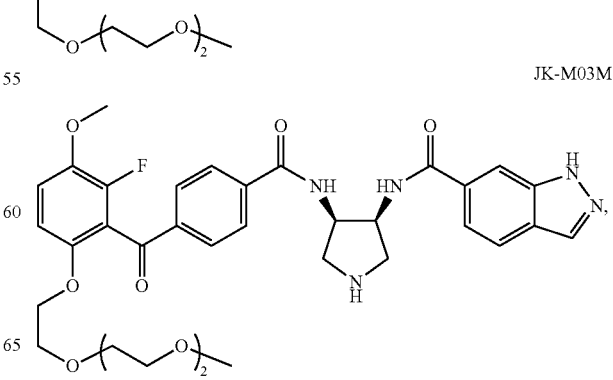

JK-M03M

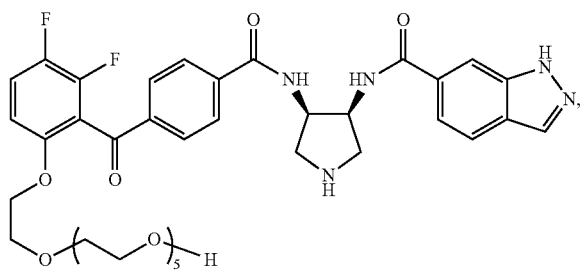

JK-06H

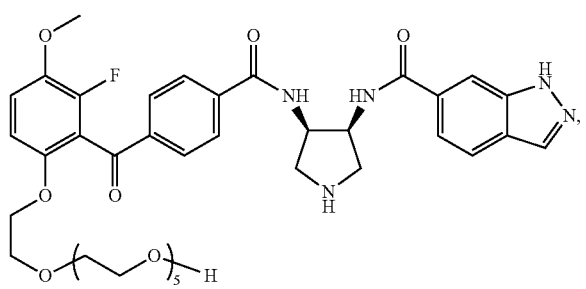

JK-M06H

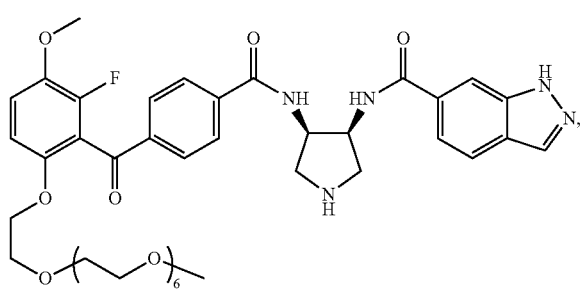

JK-07M

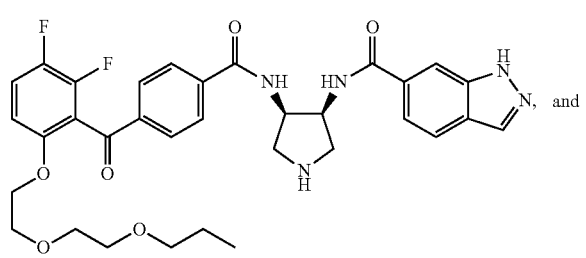

JK-02P

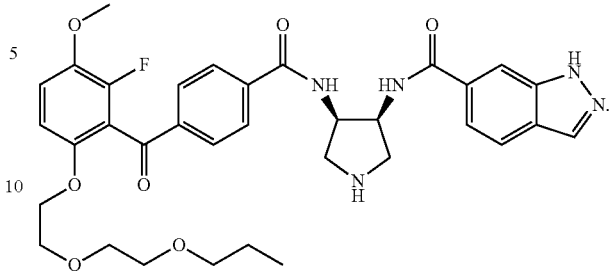

JK-M02P

The water solubility of these preferred compounds is much higher than that of compound 46. Specifically, the water solubility of JK-02H is about 5 times higher than that of compound 46; the water solubility of JK-03M is about 4 times higher than that of compound 46; the water solubility of JK-06H is about 10 times higher than that of compound 46; the water solubility of JK-07M is about 8 times higher than that of compound 46; and the water solubility of JK-02P is about 3 times higher than that of compound 46.

In a study of the therapeutic effect on hyperalgesia induced by Freund's complete adjuvant (CFA) in rats, compound JK-02H exhibited an excellent anti-hyperalgesia effect at both doses of 20 mg/kg and 5 mg/kg in comparison with the vehicle; while compound 46 exhibited an anti-hyperalgesia effect only at a dose of 40 mg/kg, but it barely showed any anti-hyperalgesia effect at a dose of 10 mg/kg.

A person skilled in the art will understand that the compounds with a chiral center disclosed in the present application can be present in the form of an enantiomer or a racemate, and that some compounds have more than one crystalline form. The present invention contemplates any racemate, enantiomer, polymorph, or stereoisomer of the compounds disclosed herein, or a mixture thereof.

Specifically, the present invention provides the following preferred compounds:

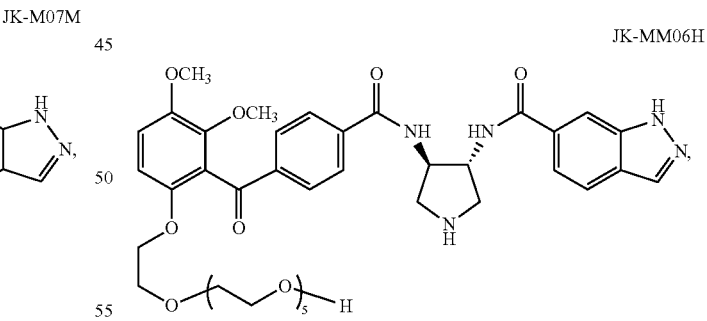

JK-MM06H

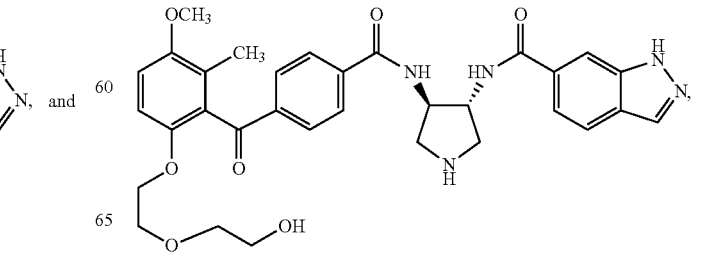

JK-MM02H

-continued

JK-E03M

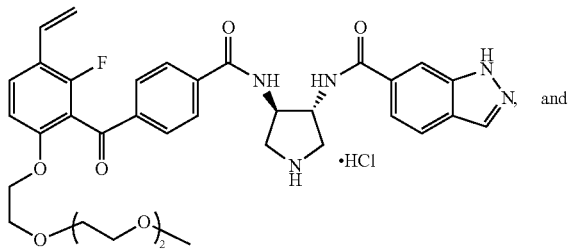

and

JK-PM06H

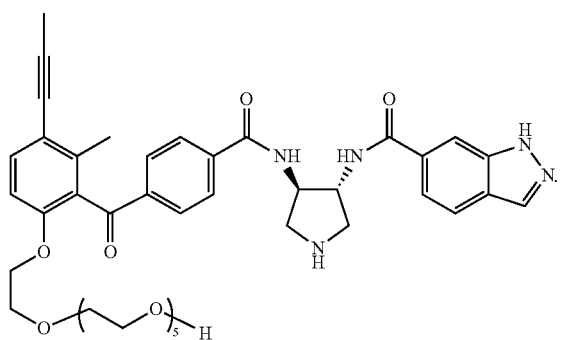

When a compound is basic enough to a form acid addition salt, the compound can be used in the form of a salt. Acceptable salts are acid addition salts formed with physiologically acceptable organic acids, such as toluene sulfonate, mesylate, acetate, propionate, hydroxyacetate, pyruvate, oxalate, malate, maleate, fumarate, cinnamate, mandelate, mesylate, esylate, p-tosylate, salicylate, citrate, malonate, tartrate, succinate, benzoate, ascorbate, α-ketoglutarate, α-glycerophosphate and the like; or acid addition salts formed with physiologically acceptable inorganic acids, such as hydrochloride, hydrobromide, sulfate, nitrate, phosphate, bicarbonate, carbonate and the like.

In another aspect, the present invention provides use of the compound of Formula I or the pharmaceutically acceptable salt thereof in the manufacture of a medicament for treating pain.

The compound of the present invention can be used for treating various pain, which includes, but is not limited to chronic pain, neuropathic pain, acute pain, cancer pain, rheumatoid arthritis pain, migraine, visceral pain and the like. The compound of the present invention can be used as an analgesic drug in general anesthesia and supervision of anesthesia nursing. Moreover, the compound of the present invention is often used in combination with drugs having different properties, so as to achieve a balance needed to maintain the state of anesthesia (such as amnesia, analgesia, muscle relaxation and sedation). The drugs for use in combination with the compound of the present invention include inhalant anesthetics, hypnotics, anxiolytics, neuromuscular blocking agents and opioids.

The compound of the present invention can be administered in different doses and different frequencies, depending on, e.g., the health condition, age, weight, gender, etc. of the subject to be treated.

In another aspect, the present invention provides a pharmaceutical composition comprising the compound of Formula I or the pharmaceutically acceptable salt thereof and one or more pharmaceutically acceptable carriers.

The carries(s) should be tolerable to the subject to be treated, and can deliver the compound to the affected area.

A preparation of the pharmaceutical composition described in the present application can be prepared by any method known in the field of pharmacy. Generally, the preparation method comprises the following steps: combining the active ingredient with a carrier or one or more other adjuvants, and packaging the resulting product as a desired single-dose or multi-dose unit, if necessary. In addition to the active ingredient, the pharmaceutical composition can further comprise one or more other pharmaceutically active agents, or the pharmaceutical composition can be used simultaneously or sequentially with one or more other pharmaceutically active agents.

The pharmaceutical composition of the present invention can be prepared, packaged or sold in the form of a sterile injectable aqueous or oily suspension or solution. The suspension or solution can be formulated according to known techniques, and in addition to the active ingredient, can contain other ingredients, such as a dispersant, a moistening agent, a suspending agent, etc. The sterile injectable preparation can be formulated using a nontoxic diluent or solvent (such as water or 1,3-butylene glycol). Other acceptable diluents and solvents include, but are not limited to Ringer's solution, isotonic sodium chloride solution, monoglyceride or diglyceride, etc.

A controlled release or sustained release preparation of the pharmaceutical composition can be prepared according to conventional techniques. The controlled release of the active ingredient can be induced by various factors, such as pH, temperature, enzyme, water, or other physiological conditions or compounds.

A suitable pharmaceutical composition comprising the compound of the present invention can be administered through conventional routes, such as oral, topical, parenteral, buccal, nasal, vaginal or rectal administration or administration via inhalation. Accordingly, the compound of the present invention can be formulated as various forms, such as tablet, capsule, aqueous or oily solution, suspension, emulsion, cream, ointment, gel, nasal spray, suppository, fine powder or aerosol for inhalation, as well as sterile aqueous or oily solution or suspension or sterile cream for parenteral administration (including intravenous injection, intramuscular injection or infusion), through methods known in the art.

In another aspect, the present invention provides a method for treating pain, comprising administering to a subject in need thereof the compound of Formula I or the pharmaceutically acceptable salt thereof in an amount effective to relieve pain, or the pharmaceutical composition comprising the compound of Formula I or the pharmaceutically acceptable salt thereof in an amount effective to relieve pain.

The treatment method using the compound of the present invention or the pharmaceutically acceptable salt thereof can be used in the treatment or prevention of pain in a mammal, including a human.

In another aspect, the present invention provides a method for preparing the compound of Formula I, comprising the following steps:

a) preparing methyl 4-[(2-R$_1$-3-R$_2$-6-hydroxy)benzoyl]benzoate (intermediate 3) according to the following scheme:

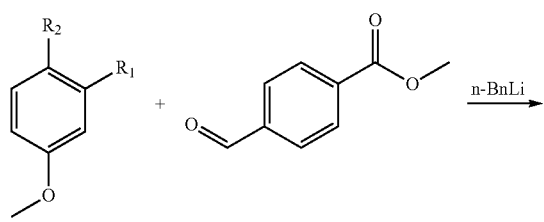
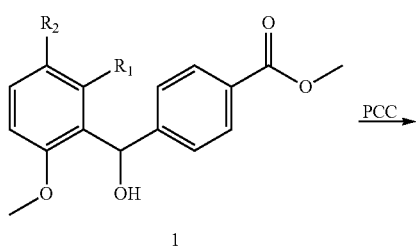
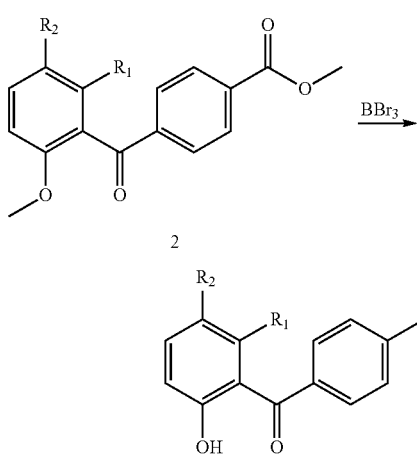
b) preparing 1-N-tert-butyloxycarbonyl-3,4-diaminopyrrolidine (intermediate 10) according to the following scheme:
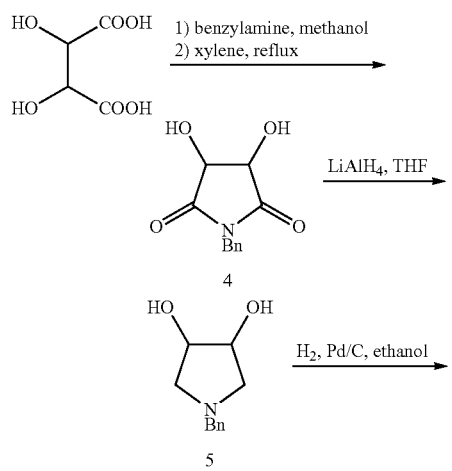
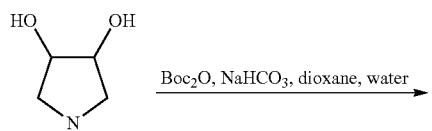
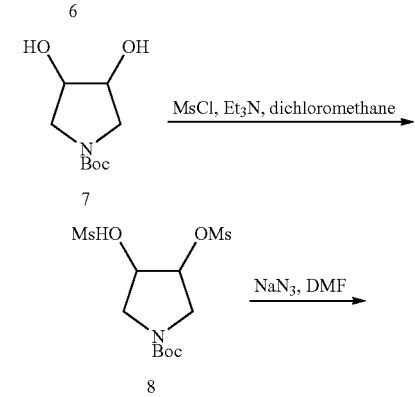
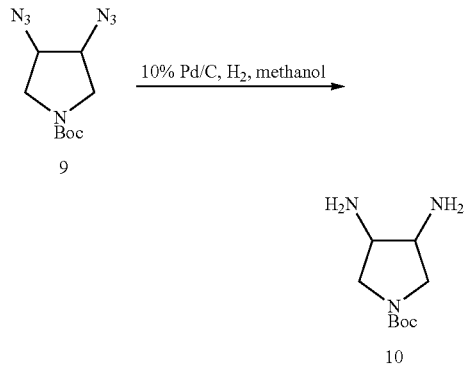
c) preparing 1H-indazole-6-carboxylic acid (intermediate 13) according to the following scheme:
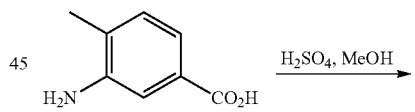
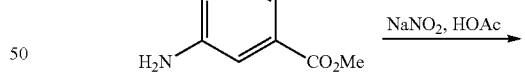
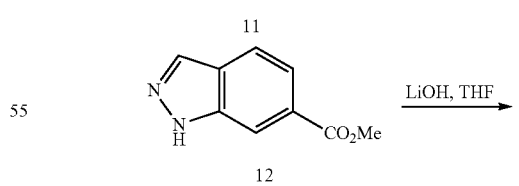
d) preparing the compound of Formula (I) according to the following scheme:

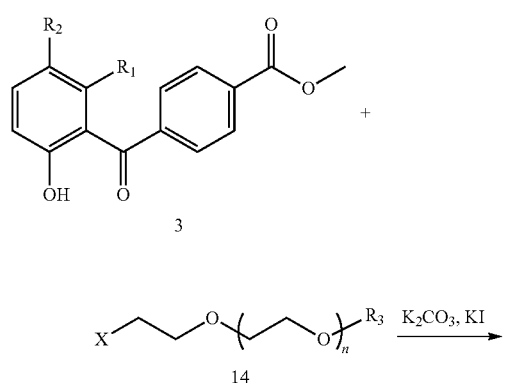
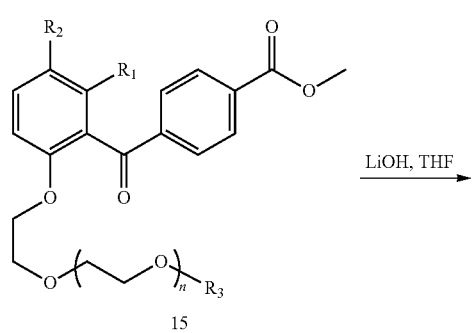
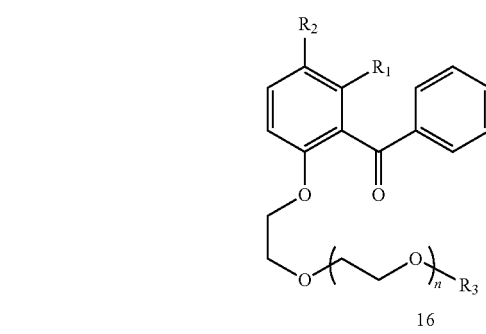
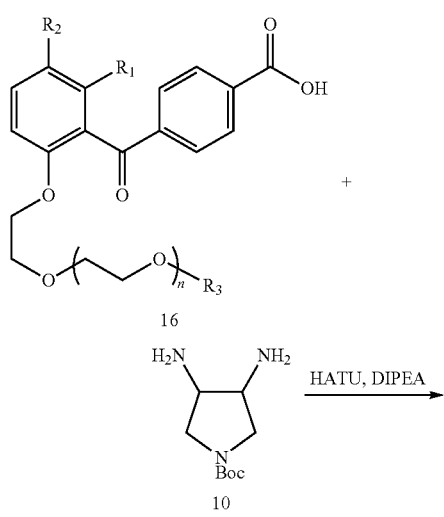
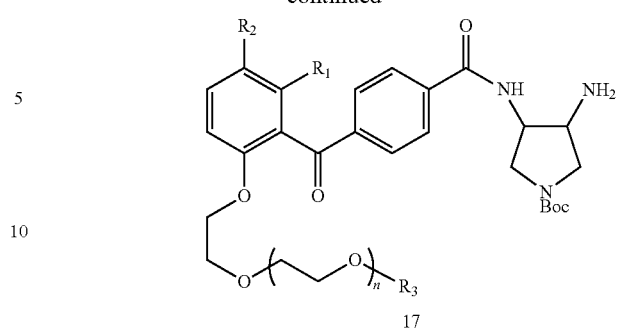
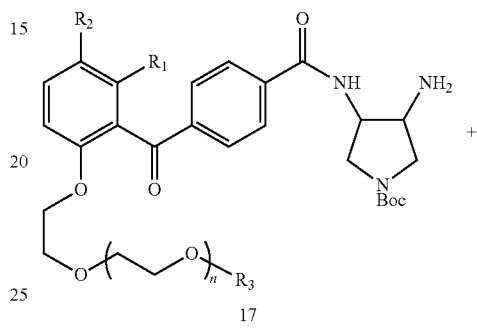
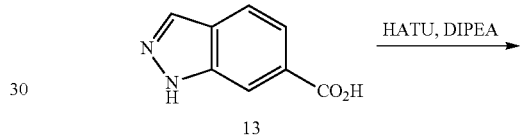
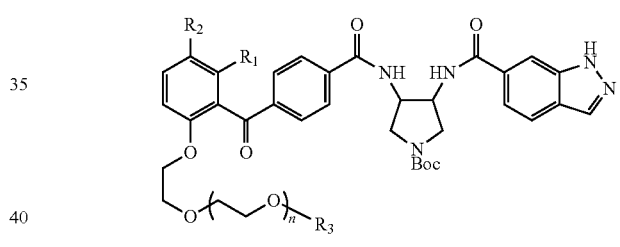
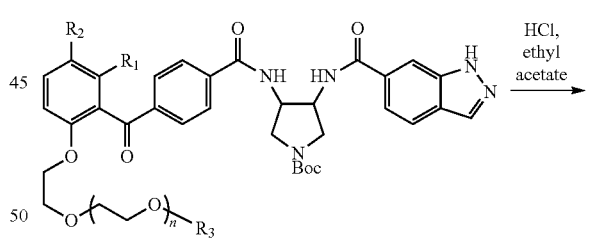
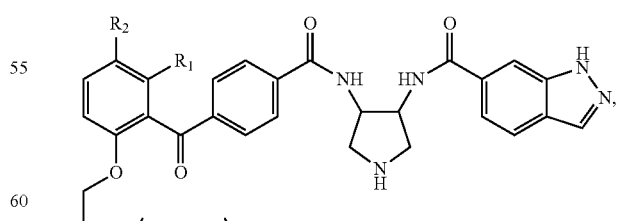
wherein X is halogen, preferably Cl or Br; and $R_1$, $R_2$, $R_3$ and n are as defined above.

Specifically, the present invention provides a method for preparing the compound of Formula I or the pharmaceutically acceptable salt thereof, comprising the following steps:

(1) performing a nucleophilic substitution reaction between compound 3

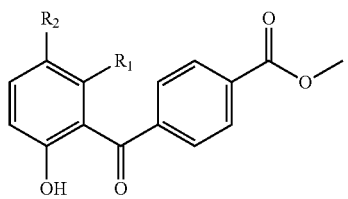

3 and compound 14

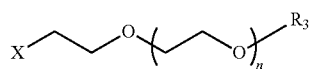

14 in the presence of a base to obtain compound 15,

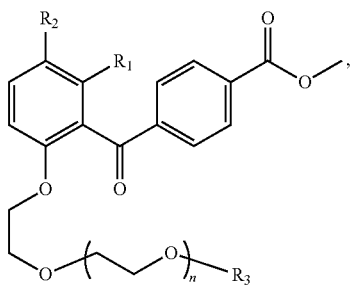

15 wherein X is a chlorine, bromine, or iodine atom, and $R_1$, $R_2$, $R_3$ and n are as defined above;

preferably, the nucleophilic substitution reaction is carried out in an organic solvent selected from the group consisting of acetonitrile, propionitrile, dimethyl formamide (DMF), dimethyl acetamide, 1,3-dimethyl-2-imidazolidinone (DMI), dimethyl sulfoxide (DMSO), hexamethylphosphoric triamide (HMPA), tetrahydrofuran, dioxane, acetone, toluene, xylene, diethyl ether, n-propyl ether, isopropyl ether, methyl tert-butyl ether, n-hexane, cyclohexane, methylcyclohexane and n-heptane, as well as any combinations thereof in any ratios; preferably, the base is selected from the group consisting of potassium carbonate, sodium carbonate, cesium carbonate, calcium carbonate, potassium hydroxide, sodium hydroxide, lithium hydroxide, calcium hydroxide, sodium hydride, potassium hydride, calcium hydride, metallic sodium, metallic potassium, sodium methoxide, sodium ethoxide, potassium tert-butoxide, butyl lithium, phenyl lithium, lithium diisopropylamide (LDA), lithium hexamethyldisilazide (LiHMDS), dimethylamine, diethylamine, triethylamine, diisopropylethylamine, piperidine, pyridine, 1,8-diazabicyclo[5.4.0]undec-7-ene (DBU), 1,5-diazabicyclo[4.3.0]non-5-ene (DBN), tetrabutylammonium hydroxide and combinations thereof;

(2) performing a hydrolysis reaction on compound 15 in the presence of a base to obtain compound 16,

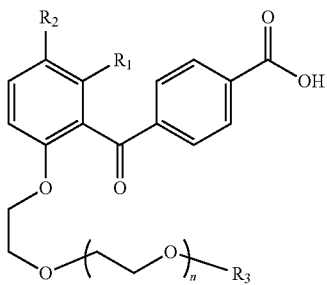

16 wherein $R_1$, $R_2$, $R_3$ and n are as defined above; preferably, the hydrolysis reaction is carried out in an organic solvent selected from the group consisting of water, methanol, ethanol, n-propanol, isopropanol, n-butanol, isobutanol, tert-buanol, tetrahydrofuran, acetonitrile, propionitrile, DMF, dimethyl acetamide, DMI, DMSO, HMPA, tetrahydrofuran, dioxane and acetone, as well as any combinations thereof in any ratios; preferably, the base is selected from the group consisting of potassium hydroxide, sodium hydroxide, lithium hydroxide, calcium hydroxide, barium hydroxide, cupric hydroxide, aluminum trichloride, boron trichloride, aluminum tribromide, boron tribromide, sodium cyanide, potassium cyanide, cesium carbonate, cupric carbonate, lithium iodide, sodium borohydride, sodium hydride, potassium hydride, calcium hydride and combinations thereof;

(3) performing an amidation reaction between compound 16 and compound 10

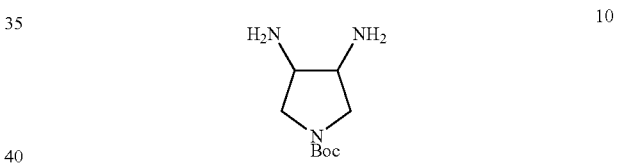

10 in the presence of a condensing agent to obtain compound 17;

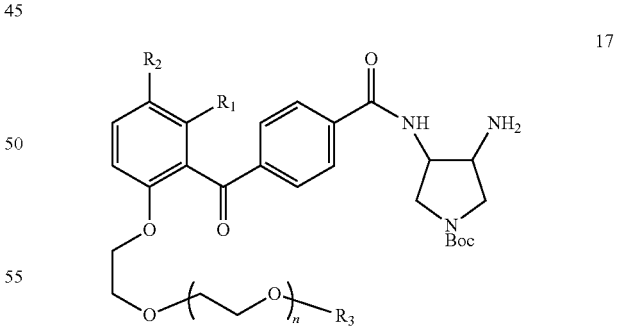

17 wherein $R_1$, $R_2$, $R_3$ and n are as defined above; preferably, the amidation reaction is carried out in an organic solvent selected from the group consisting of toluene, xylene, chlorobenzene, acetonitrile, tetrahydrofuran, dioxane, dichloromethane, trichloromethane, carbon tetrachloride, diethyl ether, n-propyl ether, isopropyl ether, methyl tert-butyl ether, n-hexane, cyclohexane, methylcyclohexane and n-heptane, as well as any combinations thereof in any ratios; preferably, the condensing agent is selected from the group consisting of N-hydroxy-7-azobenzotriazole (HOAt), 1-hydroxybenzotriazole (HOBt), 2-(7-azobenzotriazolyl)-N,N,N',N'-tetramethyluronium hexafluorophosphate (HATU), benzotriazole-N,N,N',N'-tetramethyluronium hexafluorophosphate (HBTU), bis(2-oxo-3-oxazolidinyl)phosphinic chloride (BOP—Cl), 1H-benzotriazol-1-oxytri(1-pyrrolidino)phosphonium hexafluorophosphate (PyBOP), 1,3-dicyclohexylcarbodiimide (DCC), N,N'-carbonyldiimidazole (CDI), 1-ethyl-3-(3-dimethylaminopropyl)carbodiimide (EDC), N,N'-diisopropylcarbodiimide (DIC), 4-dimethylaminopyridine (DMAP) and combinations thereof;

(4) performing an amidation reaction between compound 17 and compound 13

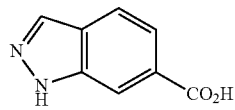

in the presence of a condensing agent to obtain compound 18;

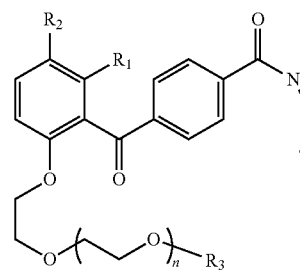

wherein Boc represents the protecting group tert-butyloxycarbonyl, and $R_1$, $R_2$, $R_3$ and n are as defined above; preferably, the amidation reaction is carried out in an organic solvent selected from the group consisting of toluene, xylene, chlorobenzene, acetonitrile, tetrahydrofuran, dioxane, dichloromethane, trichloromethane, carbon tetrachloride, diethyl ether, n-propyl ether, isopropyl ether, methyl tert-butyl ether, n-hexane, cyclohexane, methylcyclohexane and n-heptane, as well as any combinations thereof in any ratios; preferably, the condensing agent is selected from the group consisting of HOAt, HOBt, HATU, HBTU, BOP-Cl, PyBOP, DCC, CDI, EDC, DIC, DMAP and combinations thereof; and (5) performing a deprotection reaction on compound 18 in the presence of a deprotecting agent to obtain the compound of Formula I, and optionally further processing to obtain the pharmaceutically acceptable salt thereof, preferably, the deprotection reaction is carried out in an organic solvent selected from the group consisting of toluene, xylene, chlorobenzene, acetonitrile, tetrahydrofuran, dioxane, dichloromethane, trichloromethane, carbon tetrachloride, diethyl ether, n-propyl ether, isopropyl ether, methyl tert-butyl ether, n-hexane, cyclohexane, methylcyclohexane and n-heptane, as well as any combinations thereof in any ratios; preferably, the deprotecting agent is selected from the group consisting of trifluoroacetic acid, hydrochloric acid, hydrobromic acid, hydriodic acid, phosphoric acid, sulfuric acid, methanesulfonic acid, p-toluene sulfonic acid, acetyl chloride, aluminum trichloride, and boron trifluoride.

The present invention also provides novel intermediates for preparing the compound of Formula I. The intermediates are compounds of Formulae 15, 16, 17 and 18:

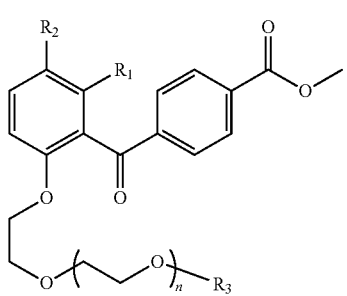

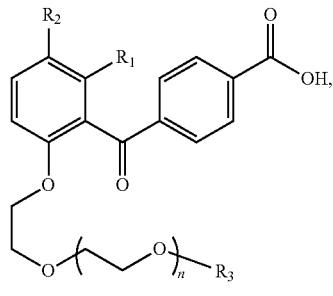

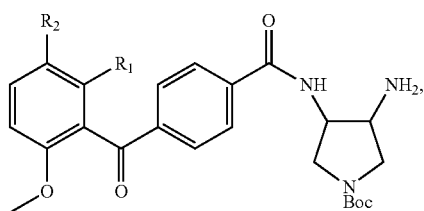

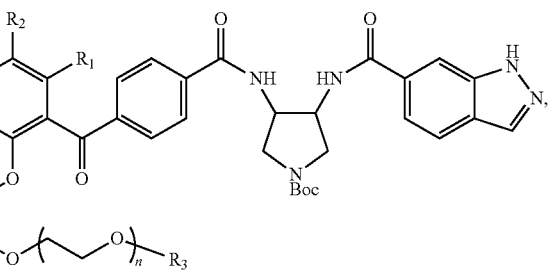

wherein Boc, $R_1$, $R_2$, $R_3$ and n are as defined above.

DEFINITIONS

As used herein, the term "analog" refers to a compound which is structurally similar to, but is not necessarily an isomer of another compound.

As used herein, the term "effective amount" refers to an amount enough to produce a desired effect.

As used herein, the term "inhibit (inhibiting, inhibition, or inhibitory)" refers to the capability of a compound in reducing or preventing the function as described.

As used herein, the term "alkyl" refers to a straight or branched alkyl group.

As used herein, the term "$C_1$-$C_6$ alkyl" refers to a straight or branched alkyl group having 1-6 carbon atoms. Generally, $C_1$-$C_6$ alkyl includes, but is not limited to: methyl, ethyl, n-propyl, isopropyl, n-butyl, isobutyl, sec-butyl, tert-butyl, pentyl, hexyl and the like.

As used herein, the term "alkenyl" refers to an alkene-type unsaturated straight or branched hydrocarbyl having at least one double bond.

As used herein, the term "$C_2$-$C_6$ alkenyl" refers to an alkene-type unsaturated straight or branched hydrocarbyl having 2-6 carbon atoms and at least one double bond. Generally, $C_2$-$C_6$ alkenyl includes, but is not limited to: ethenyl, 1-propenyl, 2-propenyl, 1,3-butadienyl, 1-butenyl, hexenyl, pentenyl and the like.

As used herein, the term "alkynyl" refers to an unsaturated straight or branched hydrocarbyl having at least one triple bond.

As used herein, the term "$C_2$-$C_6$ alkynyl" refers to an unsaturated straight or branched hydrocarbyl having 2-6 carbon atoms and at least one triple bond. Generally, $C_2$-$C_6$ alkynyl includes, but is not limited to: ethynyl, 1-propynyl, 2-propynyl, 1-butynyl, 2-butynyl, 1-pentynyl and the like.

As used herein, the term "$C_3$-$C_6$ cycloalkyl" represents cyclopropyl, cyclobutyl, cyclopentyl, cyclohexyl and the like.

As used herein, the term "aryl" refers to a monocyclic or bicyclic $C_5$-$C_{10}$ carbocyclic system having one or two aromatic rings, which includes, but is not limited to: phenyl, benzyl, naphthyl, tetrahydronaphthyl, indanyl, indenyl and the like.

As used herein, the term "heteroaryl" refers to a monocyclic or bicyclic system having one or two aromatic rings, in which 1-3 heteroatoms selected from the group consisting of nitrogen, oxygen and sulfur are contained in addition to carbon atoms. Examples of heteroaryl include, but are not limited to: furyl, thienyl, pyridyl and the like.

As used herein, the term "heterocyclyl" refers to a monocyclic or bicyclic system having carbon atoms and 1-3 heteroatoms selected from the group consisting of nitrogen, oxygen and sulfur.

Normally, not all the intermediates were structurally characterized, and mass spectrometry (MS) or nuclear magnetic resonance spectrometry (NMR) was generally employed to assess the purity of the compounds.

As used herein, the abbreviations have the following meanings: $CDCl_3$: deuterated chloroform; DCM: dichloromethane; DMF: N,N-dimethyl formamide; HATU: 2-(7-azobenzotriazolyl)-N,N,N',N'-tetramethyluronium hexafluorophosphate; DIPEA: N,N-Diisopropylethylamine; DMSO: dimethyl sulfoxide; NMR: nuclear magnetic resonance.

The present invention is now described with reference to the following examples. These examples are provided merely for the purpose of illustration, and are not intended to limit the scope of the present invention.

3,4-difluoroanisole, 3-amino-4-methylbenzoic acid, 3-fluoro-4-methoxyphenol, 3,4-dimethoxyphenol, 2-fluoro-4-methoxybenzaldehyde, m-methylanisole, 2-butynoic acid used in the examples were purchased from J&K Scientific; hexaethylene glycol and heptaethylene glycol monomethyl ether were purchased from Jiaxing Biomatrik Biotechnology Co., Ltd.; methyl p-formylbenzoate was purchased from Shanghai Bangcheng Chemical Co., Ltd.; and the remaining reagents were all purchased from Sinopharm Chemical Reagent Beijing Co., Ltd.

EXAMPLES

Example 1: The Preparation of (3R,4R)-3-{4-[2,3-difluoro-6-(5-hydroxy-3-oxapentan-1-oxy)]benzoyl}benzamido-4-(1H-indazole-6-carboxamido)pyrrolidine hydrochloride (JK-02H)

Intermediate (1A)

Methyl 4-[(2,3-difluoro-6-methoxyphenyl)hydroxymethyl]benzoate

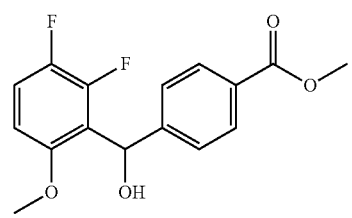

1A 2.5 M n-butyl lithium (61.6 mL, 0.154 mol) was added to a solution of 3,4-difluoroanisole (20.0 g, 0.139 mol) in anhydrous tetrahydrofuran (500 mL) which was cooled to −78° C., and the reaction mixture was stirred for 2 h. A solution of methyl p-formylbenzoate (25.2 g, 0.154 mol) in anhydrous tetrahydrofuran (500 mL) was added, and the reaction mixture was warmed slowly to room temperature over 10 h. Distilled water (1.0 L) was added to quench the reaction, and the resulting reaction mixture was extracted with ethyl acetate (3×1.0 L). The combined organic layer was dried over anhydrous sodium sulfate and filtered, and the filtrate was concentrated under reduced pressure. The residue was separated on a silica gel column to obtain intermediate (1A) as a light yellow solid (29.4 g, yield: 68.6%).

MASS (ESI+) m/z=165 (M+H)$^+$.

$^1$H NMR (400 MHz, $CDCl_3$): 3.78 (s, 3H), 3.88 (s, 3H), 4.30 (d, 1H), 6.36 (d, 1H), 6.71 (d, 1H), 7.23 (d, 1H), 7.37 (d, 2H), 7.94 (d, 2H).

Intermediate (2A)

Methyl 4-[(2,3-difluoro-6-methoxy)benzoyl]benzoate

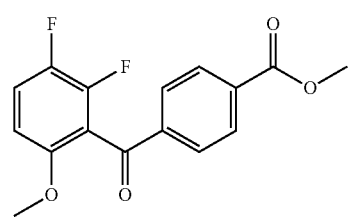

2A

A solution of intermediate (1A) (25 g, 81.1 mmol) in dichloromethane (250 mL) was added to a solution of pyridinium chlorochromate (PCC, 26.2 g, 121.7 mmol) in dichloromethane (500 mL) at room temperature under a nitrogen atmosphere, and the reaction mixture was stirred at room temperature for 4 h. The reaction mixture was filtered, and the filtrate was concentrated under reduced pressure. The residue was separated on a silica gel column to obtain intermediate (2A) as a light yellow solid (20.8 g, yield: 83.7%).

MASS (ESI+) m/z=309 (M+H)+.

$^1$H NMR (400 MHz, CDCl$_3$): 3.69 (s, 3H), 3.94 (s, 3H), 6.95 (d, 1H), 7.35 (d, 1H), 7.82 (d, 2H), 8.09 (d, 2H).

Intermediate (3A)

Methyl 4-[(2,3-difluoro-6-hydroxy)benzoyl]benzoate

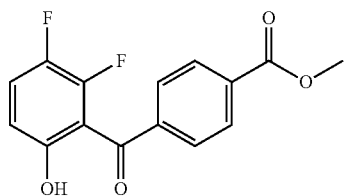

(3A)

Boron tribromide (24.5 g, 97.8 mmol) was added to a solution of intermediate (2A) (15 g, 49.0 mmol) in dichloromethane (500 mL) at −78° C., and the reaction mixture was stirred for 2 h. Distilled water (250 mL) was added. After liquid separation, the water layer was extracted with dichloromethane (2×250 mL), and the combined organic layer was washed with saturated brine (500 mL), dried over anhydrous sodium sulfate, and filtered. The filtrate was concentrated under reduced pressure, and the residue was separated on a silica gel column to obtain intermediate (3A) as a light yellow solid (13.6 g, yield: 95.0%).

MASS (ESI+) m/z=307 (M+H)$^+$.

$^1$H NMR (400 MHz, CDCl$_3$): 3.99 (s, 3H), 6.89 (d, 1H), 7.26 (d, 1H), 7.74 (d, 2H), 8.18 (d, 2H), 11.29 (s, 1H).

Intermediate ((3R,4R)-4)

(3R,4R)-1-N-benzyl-3,4-dihydroxypyrrolidine-2,5-dione

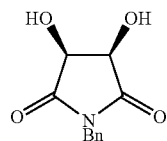

(3R,4R)-4

Benzylamine (107.2 g, 1.0 mol) was slowly added to a solution of L-(+)-tartaric acid (150.1 g, 1.0 mol) in 50% methanol/water (200 mL). The reaction mixture was heated at 50° C. with stirring until it turned clear, and was then concentrated under reduced pressure. Xylene (3 L) was added to the residue, and the reaction mixture was refluxed in an oil bath for 8 h. The resulting reaction mixture was cooled, followed by concentration under reduced pressure, using anhydrous ethanol (2×150 mL) to remove the trace amount of xylene. Anhydrous ethanol (700 mL) was added to the residue, and the resulting mixture was then heated to reflux for 30 min with stirring. The mixture was cooled to room temperature and filtered. The filter cake was washed with anhydrous ethanol (3×100 mL), and dried to obtain intermediate ((3R,4R)-4) as white needles (153.9 g, yield: 69.6%). The filtrate and wash solution were combined, and concentrated to 300 mL. Activated carbon (30 g) was added. The resulting mixture was stirred at reflux for 30 min, and filtered while hot. The filter cake was washed with hot ethanol (100 mL). The filtrate and wash solution were combined, stood for crystallization under cooling, and filtered to further obtain intermediate ((3R,4R)-4) (33.4 g, 15.1%). The total amount of intermediate ((3R,4R)-4) obtained from the above two steps was 187.3 g, and the yield in total was 84.7%.

MASS (ESI+) m/z=222 (M+H)$^+$.

$^1$H NMR (400 MHz, DSO-d$_6$): 4.38 (d, 2H), 4.53 (d, 1H), 4.58 (d, 1H), 6.29 (d, 2H), 7.24 (m, 2H), 7.27 (m, 1H), 7.33 (m, 2H).

Intermediate ((3S,4S)-5)

(3S,4S)-1-N-benzyl-3,4-dihydroxypyrrolidine

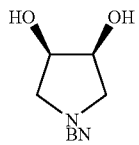

(3S,4S)-5

Under a nitrogen atmosphere, intermediate ((3R,4R)-4) (132.7 g, 0.6 mol) was slowly added to a solution of LiAlH$_4$ (61.2 g, 1.6 mol) in tetrahydrofuran (3.6 L) which was cooled to 0° C. The reaction mixture was refluxed for 12 h, and cooled to room temperature. Ethyl acetate (144 mL) was added dropwise to the reaction mixture in a cold water bath. Distilled water (61.2 mL), 5% NaOH (61.2 mL) and distilled water (183.6 mL) were sequentially added dropwise under vigorous stirring. The mixture was filtered, and the filter cake was washed with hot tetrahydrofuran (2×1.2 L). The filtrate and wash solution were combined and concentrated under reduced pressure. The residue was separated on a silica gel column to obtain a light yellow oil, which was then recrystallized with ethyl acetate to obtain intermediate ((3S,4S)-5) as a white solid (82.3 g, yield: 71.0%).

MASS (ESI+) m/z=194 (M+H)$^+$.

$^1$H NMR (400 MHz, DSO-d$_6$): 2.30 (dd, 2H), 2.74 (dd, 2H), 3.46 (d, 1H), 3.57 (d, 1H), 3.84 (m, 2H), 4.84 (br s, 2H), 7.20-7.35 (m, 5H).

Intermediate ((3S,4S)-6)

(3S,4S)-3,4-dihydroxypyrrolidine

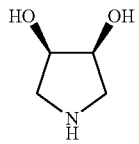

(3S,4S)-6

Intermediate ((3S,4S)-5) (77.3 g, 0.4 mol) was dissolved in an aqueous solution of ethanol (80%), to which 10% Pd/C (7.0 g) was added. Hydrogen (0.07 MPa) was supplied, and the reaction was kept for 2 days at room temperature. The catalyst was filtered off, and the filtrate was concentrated under reduced pressure. Anhydrous ethanol (2×250 mL) was used to remove the trace amount of water from the residue to obtain intermediate ((3S,4S)-6) as a yellow oil (37.5 g, yield: 90.9%).

MASS (ESI+) m/z=104 (M+H)+.

$^1$H NMR (400 MHz, DSO-d$_6$): 2.60 (m, 2H), 3.02 (m, 2H), 3.83 (m, 2H), 4.81 (br s, 3H).

Intermediate ((3S,4S)-7)

(3S,4 S)-1-N-tert-butyloxycarbonyl-3,4-dihydroxypyrrolidine

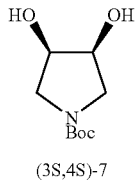 [SMILES: CC(C)(C)OC(=O)N1C[C@@H](O)[C@@H](O)C1]

(3S,4S)-7

Di-tert-butyl dicarbonate (98.2 g, 0.45 mol) was added dropwise to an solution of intermediate ((3S,4S)-6) (30.9 g, 0.30 mol) and sodium bicarbonate (218.9 g, 25.8 mol) in 50% dioxane/water under vigorous stirring. The reaction mixture was stirred at room temperature for 2 h and filtered. The filtrate was concentrated under reduced pressure, and the residue was separated on a silica gel column to obtain intermediate ((3S,4S)-7) as a white solid (51.6 g, yield: 84.6%).

MASS (ESI+) m/z=204 (M+H)+.

$^1$H NMR (400 MHz, DSO-d$_6$): 1.39 (s, 9H), 3.11 (dd, 2H), 3.34 (dd, 2H), 3.86 (m, 2H), 5.06 (d, 2H).

Intermediate ((3S,4S)-8)

(3S,4 S)-1-N-tert-butyloxycarbonyl-3,4-dimethylsulfonyloxypyrrolidine

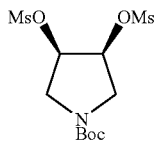

(3S,4S)-8

Triethylamine (140 mL, 1.0 mol) and methanesulfonyl chloride (58 mL, 0.75 mol) were added to a solution of intermediate ((3S,4S)-7) (50.8 g, 0.25 mol) in dichloromethane (1.6 L) which was cooled to 0° C. After the ice-salt bath was removed, the reaction mixture was naturally warmed to room temperature, at which it was further stirred for 6 h. The reaction mixture was washed successively with saturated ammonium chloride solution and saturated brine, dried over anhydrous sodium sulfate, and filtered. The filtrate was concentrated under reduced pressure, and the residue was separated on a silica gel column to obtain intermediate ((3S,4S)-8) as a white solid (84.7 g, yield: 94.3%).

MASS (ESI+) m/z=360 (M+H)+.

$^1$H NMR (400 MHz, CDCl$_3$): 1.47 (s, 9H), 3.12 (s, 6H), 3.71 (m, 2H), 3.79 (d, 1H), 3.82 (d, 1H), 5.19 (br s, 2H).

Intermediate ((3R,4R)-9)

(3R,4R)-1-N-tert-butyloxycarbonyl-3,4-diazidopyrrolidine

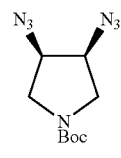

(3R,4R)-9

NaN$_3$ (143.0 g, 2.2 mol) was added to a solution of intermediate ((3S,4S)-8) (71.9 g, 0.20 mol) in DMF (1.8 L). The reaction mixture was heated at 90° C. for 24 h, and evaporated to dryness under reduced pressure. The residue was diluted with ethyl acetate (900 mL), and washed with distilled water (3×180 mL). The aqueous layer was extracted with ethyl acetate (180 mL), and the combined organic layer was washed with saturated brine (90 mL), dried over anhydrous sodium sulfate, and filtered. The filtrate was concentrated under reduced pressure, and the residue was separated on a silica gel column to obtain intermediate ((3R,4R)-9) as a yellow oil (34.4 g, yield: 67.9%).

MASS (ESI+) m/z=254 (M+H)+.

$^1$H NMR (400 MHz, CDCl$_3$): 1.45 (s, 9H), 3.34 (m, 2H), 3.65 (m, 2H), 3.94 (m, 2H).

Intermediate ((3R,4R)-10)

(3R,4R)-1-N-tert-butyloxycarbonyl-3,4-diaminopyrrolidine

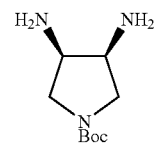

(3R,4R)-10

Intermediate ((3R,4R)-9) (30.4 g, 0.12 mol) was dissolved in anhydrous methanol (500 mL), and 10% Pd/C (12.8 g, 12 mmol) was added. Hydrogen (0.1 MPa) was supplied, and the reaction was kept for 18 h at room temperature. The catalyst was filtered off, and the filtrate was concentrated under reduced pressure to obtain intermediate ((3R,4R)-10) as a yellow oil (23.4 g, yield: 96.9%).

MASS (ESI+) m/z=202 (M+H)+.

$^1$H NMR (400 MHz, CDCl$_3$): 1.48 (s, 9H), 1.64-1.99 (m, 4H), 3.14-3.37 (m, 2H), 3.38-3.52 (m, 2H), 3.52-3.78 (m, 2H).

Intermediate (11)

Methyl 3-amino-4-methylbenzoate

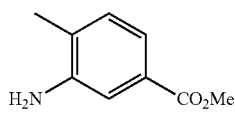
11

3-amino-4-methylbenzoic acid (60.5 g, 0.40 mol) was dissolved in anhydrous methanol (1.5 L), and the resulting solution was cooled to 5° C. with stirring. Thionyl chloride (103.6 g, 0.87 mol) was slowly added dropwise, and the reaction mixture was stirred under reflux for 6 h after the addition. After cooled to room temperature, the reaction mixture was concentrated under reduced pressure, and the residue was diluted with ice water (1.2 L), followed by neutralization to pH 7.5 by adding 5% $NaHCO_3$. The aqueous layer was extracted with ethyl acetate (3×600 mL), and the combined organic layer was washed with saturated brine (2×500 mL), dried over anhydrous sodium sulfate, and filtered. The filtrate was concentrated under reduced pressure to obtain intermediate (11) as a white solid (62.7 g, yield: 94.9%).

MP 114-116° C.

$^1$H NMR (400 MHz, $CDCl_3$): 2.19 (s, 3H), 3.73 (br s, 2H), 3.87 (s, 3H), 7.09 (m, 1H), 7.34-7.37 (m, 2H).

Intermediate (12)

Methyl 1H-indazole-6-carboxylate

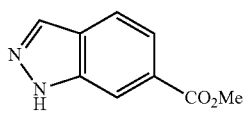
12

Intermediate (11) (57.8 g, 0.35 mol) was dissolved in glacial acetic acid (1.5 L), and a solution of $NaNO_2$ (24.2 g, 0.35 mol) in distilled water (350 mL) was slowly added dropwise. The reaction mixture was stirred at room temperature for 5 h, and concentrated under reduced pressure. Distilled water (500 mL) was added to the residue, and the mixture was extracted with ethyl acetate (3×1.0 L). The organic layer was washed with distilled water (1.5 L) and brine (1.5 L), dried over anhydrous sodium sulfate, and filtered. The filtrate was concentrated under reduced pressure to obtain intermediate (12) as a light yellow solid (49.5 g, yield: 80.8%).

MASS (ESI+) m/z=177 (M+H)$^+$.

$^1$H NMR (400 MHz, $CDCl_3$): 3.96 (s, 3H), 7.80-7.85 (m, 2H), 8.14 (s, 1H), 8.27 (s, 1H).

Intermediate (13)

1H-indazole-6-carboxylic Acid

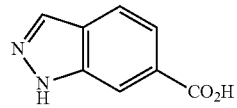
13

Intermediate (12) (44.0 g, 0.25 mol) was dissolved in tetrahydrofuran (500 mL), and an aqueous solution of 2 N LiOH (200 mL, 0.40 mol) was added. The reaction mixture was stirred at 50° C. for 4 h, and was then cooled to room temperature. Tetrahydrofuran was distilled off under reduced pressure, and the residue was diluted by adding distilled water (200 mL). The resulting mixture was acidified to pH 3.5 with 1 N HCl, and was extracted with ethyl acetate (3×500 mL). The combined organic layer was washed with brine (500 mL), dried over anhydrous sodium sulfate, and filtered. The filtrate was concentrated under reduced pressure to obtain intermediate (13) as a light yellow solid (34.7 g, yield: 85.6%).

MASS (ESI+) m/z=163 (M+H)$^+$.

$^1$H NMR (400 MHz, $CD_3OD$): 7.79-7.87 (m, 2H), 8.14 (s, 1H), 8.29 (s, 1H).

Intermediate (15-02H)

Methyl 4-[2,3-difluoro-6-(5-hydroxy-3-oxapentan-1-oxy)]benzoylbenzoate

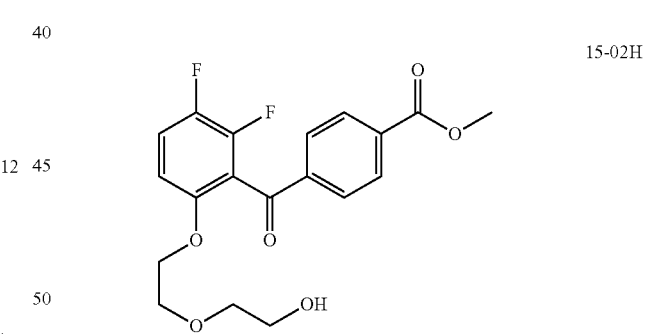
15-02H

Intermediate (3A) (6.00 g, 20.52 mmol), 2-(2-chloroethoxy)ethanol (7.67 g, 61.56 mmol), $K_2CO_3$ (8.51 g, 61.56 mmol) and KI (0.34 g, 2.05 mmol) were dissolved in DMF (125 mL), and the reaction mixture was refluxed overnight under a nitrogen atmosphere. The reaction mixture was cooled to room temperature before distilled water (100 mL) was added, and was extracted with ethyl acetate (3×200 mL). The combined organic layer was washed with saturated brine (300 mL), dried over anhydrous sodium sulfate, and filtered. The filtrate was concentrated under reduced pressure, and the residue was separated on a silica gel column to obtain intermediate (15-02H) as a light yellow solid (5.17 g, yield: 66.2%).

MASS (ESI+) m/z=381 (M+H)$^+$.

Intermediate (16-02H)

4-[2,3-difluoro-6-(5-hydroxy-3-oxapentan-1-oxy)]benzoylbenzoic acid

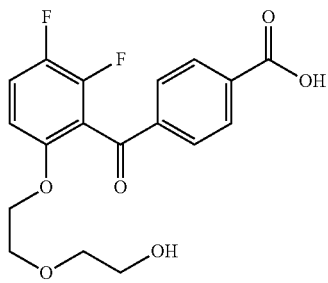

16-02H

Intermediate (15-02H) (5.00 g, 13.15 mmol) was dissolved in tetrahydrofuran (100 mL), and an aqueous solution of 2 N LiOH (42 mL, 21.00 mmol) was added. The reaction mixture was stirred at 50° C. for 4 h, and was then cooled to room temperature. Tetrahydrofuran was distilled off under reduced pressure, and the residue was diluted by adding distilled water (40 mL). The resulting mixture was acidified to pH 3.5 with 1 N HCl, and was extracted with ethyl acetate (3×100 mL). The combined organic layer was washed with brine (100 mL), dried over anhydrous sodium sulfate, and filtered. The filtrate was concentrated under reduced pressure to obtain intermediate (16-02H) as a light yellow solid (4.28 g, yield: 88.9%).

MASS (ESI+) m/z=367 (M+H)$^+$.

Intermediate (17-02H)

Tert-butyl (3R,4R)-3-amino-4-{4-[2,3-difluoro-6-(5-hydroxy-3-oxapentan-1-oxy)benzoyl]}benzamidopyrrolidine-1-carboxylate

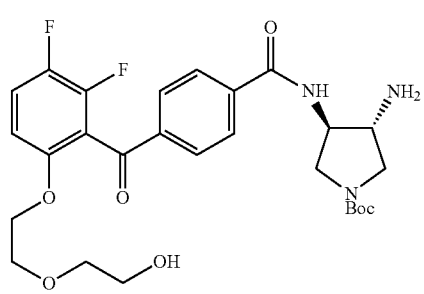

17-02H

HATU (4.57 g, 12.01 mmol) was added to a solution of intermediate (16-02H) (4.00 g, 10.92 mmol), intermediate ((3R,4R)-10) (4.40 g, 21.84 mmol) and DIPEA (2.82 g, 21.84 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (17-02H) as a light yellow solid (3.87 g, yield: 64.5%).

MASS (ESI+) m/z=550 (M+H)$^+$.

Intermediate (18-02H)

Tert-butyl (3R,4R)-3-{4-[2,3-difluoro-6-(5-hydroxy-3-oxapentan-1-oxy)]benzoyl}benzamido-4-(1H-indazole-6-carboxamido)pyrrolidine-1-carboxylate

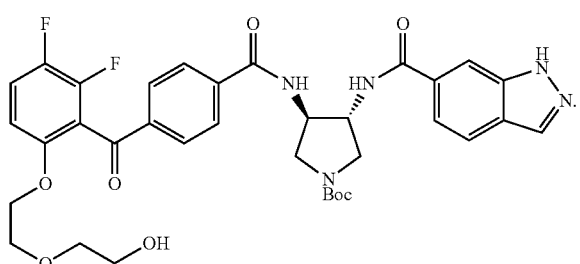

18-02H

HATU (2.67 g, 7.01 mmol) was added to a solution of intermediate (17-02H) (3.50 g, 6.37 mmol), intermediate (13) (1.14 g, 7.01 mmol) and DIPEA (2.47 g, 19.11 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (18-02H) as a light yellow solid (3.76 g, yield: 85.1%).

MASS (ESI+) m/z=694 (M+H)$^+$.

Product (JK-02H)

(3R,4R)-3-{4-[2,3-difluoro-6-(5-hydroxy-3-oxapentan-1-oxy)]benzoyl}benzamido-4-(1H-indazole-6-carboxamido)pyrrolidine hydrochloride

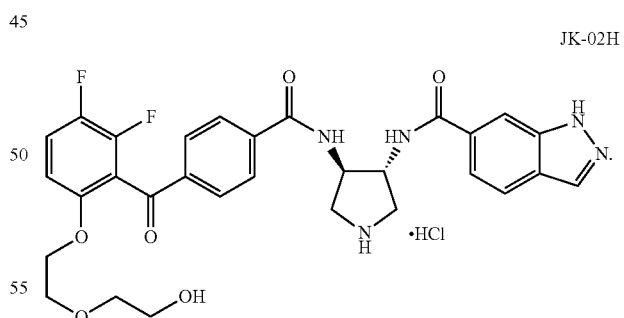

JK-02H

A solution of 4 mol/L hydrogen chloride in ethyl acetate (100 mL) was added to a solution of intermediate (18-02H) (3.50 g, 5.05 mmol) in ethyl acetate (100 mL) which was cooled to 0° C., and the reaction mixture was stirred at room temperature for 2 h. After filtration, the filter cake was washed with ethyl acetate, and dried under vacuum to obtain product (JK-02H) as a light yellow solid (2.75 g, yield: 86.4%).

MASS (ESI+) m/z=594 (M+H)$^+$.

Example 2: The Preparation of (3R,4R)-3-{4-[2,3-difluoro-6-(2,5,8-trioxadecan-10-oxy)]benzoyl}benzamido-4-(1H-indazole-6-carboxamido)pyrrolidine hydrochloride (JK-03M)

Intermediate (15-03M)

Methyl 4-{[2,3-difluoro-6-(2,5,8-trioxadecan-10-oxy)]benzoyl}benzoate

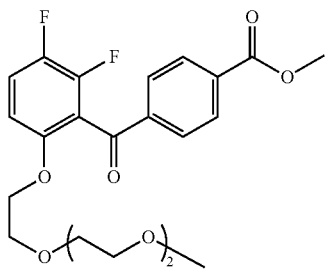

15-03M

2,5,8-trioxadecyl-10-p-toluenesulfonate

Under cooling with an ice-salt bath, a solution of p-toluenesulfonyl chloride (85.7 g, 0.45 mol) in dichloromethane (125 mL) was added dropwise to a mixed solution of triethylene glycol monomethyl ether (49.2 g, 0.30 mol) and pyridine (35.5 g, 0.45 mol), with the rate of addition controlled so that the temperature of the reaction solution was kept lower than 20° C. The reaction solution was stirred overnight at room temperature. Distilled water (100 mL) was added, and the pH of the reaction mixture was adjusted to 4.0 with a 6 N NaOH solution. After liquid separation, the organic layer was washed with distilled water (2×50 mL). Distilled water (100 mL) was added to the organic layer, and the pH was adjusted to 1.5 with a solution of 6 N HCl. After liquid separation, the organic layer was washed with distilled water (2×50 mL), dried over anhydrous sodium sulfate, and filtered. The solvent was distilled off under reduced pressure to obtain a light yellow oil (74.4 g, yield: 78.0%).

$^1$H NMR (400 MHz, CDCl$_3$): 2.46 (s, 3H), 3.38 (s, 3H), 3.54 (t, 2H), 3.62 (m, 6H), 3.70 (t, 2H), 4.17 (t, 2H), 7.35 (d, 2H), 7.81 (d, 2H).

10-bromo-2,5,8-trioxadecane

Under cooling with an ice-salt bath, lithium bromide (16.3 g, 0.19 mol) was slowly added to a solution of 2,5,8-trioxadecyl-10-p-toluenesulfonate (39.8 g, 0.13 mol) in DMF (40 mL), with the rate of addition controlled so that the temperature of the reaction solution was kept lower than 20° C. The reaction solution was vigorously stirred overnight at room temperature. Ethyl acetate (125 mL) was added, and the reaction mixture was stirred for 1 h before filtration. The filtrate was washed with distilled water (2×100 mL). The organic layer was dried over anhydrous sodium sulfate, and filtered. The filtrate was concentrated under reduced pressure, and the residue was evaporated under reduced pressure to obtain a light yellow oil (26.8 g, yield: 90.8%).

$^1$H NMR (400 MHz, CDCl$_3$): 3.34 (s, 3H), 3.42 (t, 2H), 3.49-3.53 (m, 2H), 3.59-3.66 (m, 6H), 3.77 (t, 2H).

Methyl 4-{[2,3-difluoro-6-(2,5,8-trioxadecan-10-oxy)]benzoyl}benzoate

Intermediate (3A) (6.00 g, 20.52 mmol), 10-bromo-2,5,8-trioxadecane (13.98 g, 61.56 mmol), K$_2$CO$_3$ (8.51 g, 61.56 mmol) and KI (0.34 g, 2.05 mmol) were dissolved in DMF (125 mL), and the reaction solution was refluxed overnight under a nitrogen atmosphere. The reaction solution was cooled to room temperature before distilled water (100 mL) was added, and was extracted with ethyl acetate (3×200 mL). The combined organic layer was washed with saturated brine (300 mL), dried over anhydrous sodium sulfate, and filtered. The filtrate was concentrated under reduced pressure, and the residue was separated on a silica gel column to obtain intermediate (15-03M) as a light yellow solid (6.24 g, yield: 69.4%).

MASS (ESI+) m/z=439 (M+H)$^+$.

Intermediate (16-03M)

4-{[2,3-difluoro-6-(2,5, 8-trioxadecan-10-oxy)]benzoyl}benzoic acid

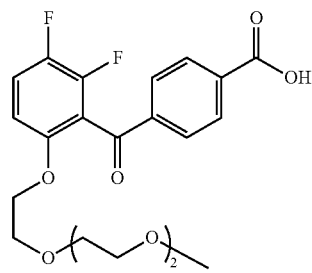

16-03M

Intermediate (15-03M) (6.00 g, 13.69 mmol) was dissolved in tetrahydrofuran (100 mL), and an aqueous solution of 2 N LiOH (44 mL, 22.00 mmol) was added. The reaction mixture was stirred at 50° C. for 4 h, and was then cooled to room temperature. Tetrahydrofuran was distilled off under reduced pressure, and the residue was diluted by adding distilled water (40 mL). The resulting mixture was acidified to pH 3.5 with 1 N HCl, and was extracted with ethyl acetate (3×100 mL). The combined organic layer was washed with brine (100 mL), dried over anhydrous sodium sulfate, and filtered. The filtrate was concentrated under reduced pressure to obtain intermediate (16-03M) as a light yellow solid (5.32 g, yield: 91.6%).

MASS (ESI+) m/z=425 (M+H)$^+$.

Intermediate (17-03M)

Tert-butyl (3R,4R)-3-amino-4-{4-[2,3-difluoro-6-(2,5,8-trioxadecan-10-oxy)]benzoyl}benzamidopyrrolidine-1-carboxylate

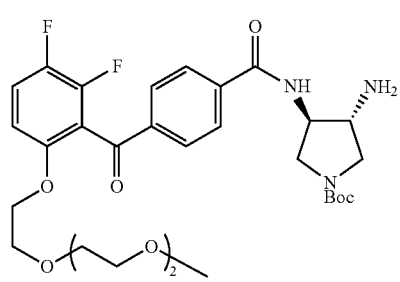

17-03M

HATU (4.57 g, 12.01 mmol) was added to a solution of intermediate (16-03M) (4.63 g, 10.92 mmol), intermediate ((3R,4R)-10) (4.40 g, 21.84 mmol) and DIPEA (2.82 g, 21.84 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (17-03M) as a light yellow solid (4.88 g, yield: 73.5%).

MASS (ESI+) m/z=608 (M+H)+.

Intermediate (18-03M)

Tert-butyl (3R,4R)-3-{4-[2,3-difluoro-6-(2,5,8-trioxadecan-10-oxy)]benzoyl}benzamido-4-(1H-indazole-6-carboxamido)pyrrolidine-1-carboxylate

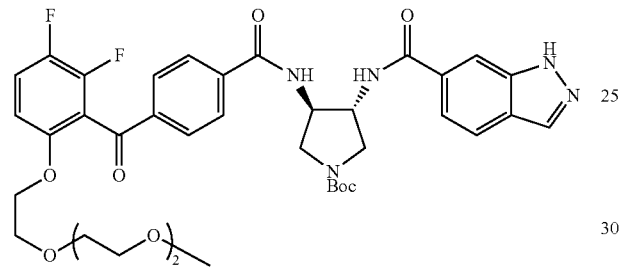

18-03M

HATU (2.67 g, 7.01 mmol) was added to a solution of intermediate (17-03M) (3.87 g, 6.37 mmol), intermediate (13) (1.14 g, 7.01 mmol) and DIPEA (2.47 g, 19.11 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (18-03M) as a light yellow solid (4.27 g, yield: 89.2%).

MASS (ESI+) m/z=752 (M+H)+.

Product (JK-03M)

(3R,4R)-3-{4-[2,3-difluoro-6-(2,5,8-trioxadecan-10-oxy)]benzoyl}benzamido-4-(1H-indazole-6-carboxamido)pyrrolidine hydrochloride

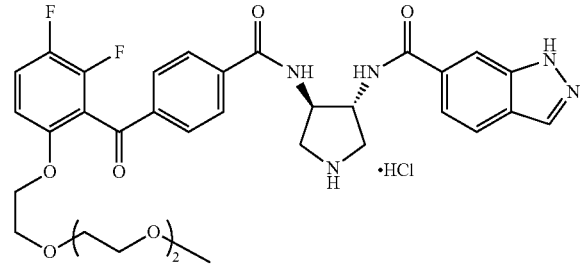

JK-03M

A solution of 4 mol/L hydrogen chloride in ethyl acetate (100 mL) was added to a solution of intermediate (18-03M) (4.00 g, 5.32 mmol) in ethyl acetate (100 mL) which was cooled to 0° C., and the reaction mixture was stirred at room temperature for 2 h. After filtration, the filter cake was washed with ethyl acetate, and dried under vacuum to obtain product (JK-03M) as a light yellow solid (3.07 g, yield: 83.9%).

MASS (ESI+) m/z=652 (M+H)+.

Example 3: The Preparation of (3R,4R)-3-{4-[2,3-difluoro-6-(17-hydroxy-3,6,9,12,15-pentaoxaheptadecan-1-oxy)]benzoyl}benzamido-4-(1H-indazole-6-carboxamido)pyrrolidine hydrochloride (JK-06H)

Intermediate (15-06H)

Methyl 4-{[2,3-difluoro-6-(17-hydroxy-3,6,9,12,15-pentaoxaheptadecan-1-oxy)]benzoyl}benzoate

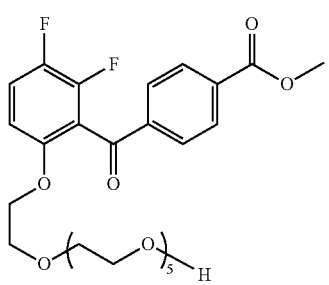

15-06H 17-hydroxy-3,6,9,12,15-pentaoxaheptadecyl-1-p-toluenesulfonate

Under cooling with an ice-salt bath, a solution of p-toluenesulfonyl chloride (85.7 g, 0.45 mol) in dichloromethane (125 mL) was added dropwise to a mixed solution of hexaethylene glycol (127.0 g, 0.45 mol) and pyridine (35.5 g, 0.45 mol), with the rate of addition controlled so that the temperature of the reaction solution was kept lower than 20° C. The reaction solution was stirred overnight at room temperature. Distilled water (100 mL) was added, and the pH of the reaction mixture was adjusted to 4.0 with a 6 N NaOH solution. After liquid separation, the organic layer was washed with distilled water (2×50 mL). Distilled water (100 mL) was added to the organic layer, and the pH was adjusted to 1.5 with a solution of 6 N HCl. After liquid separation, the organic layer was washed with distilled water (2×50 mL). The organic layer was dried over anhydrous sodium sulfate and filtered. The solvent was distilled off under reduced pressure to obtain a light yellow oil (75.4 g, yield: 38.4%).

1H NMR (400 MHz, CDCl3): 2.37 (s, 3H), 2.90 (s, 1H), 3.50-3.62 (m, 22H), 4.08 (t, 2H), 7.27 (d, 2H), 7.72 (d, 2H).

17-bromo-3,6,9,12,15-pentaoxaheptadecan-1-ol

Under cooling with an ice-salt bath, lithium bromide (16.3 g, 0.19 mol) was slowly added to a solution of 17-hydroxy-3,6,9,12,15-pentaoxaheptadecyl-1-p-toluenesulfonate (56.7 g, 0.13 mol) in DMF (40 mL), with the rate of addition controlled so that the temperature of the reaction solution was kept lower than 20° C. The reaction solution was vigorously stirred overnight at room temperature. Ethyl acetate (125 mL) was added, and the reaction solution was stirred for 1 h before filtration. The filtrate was washed with distilled water (2×100 mL). The organic layer was dried over anhydrous sodium sulfate and filtered. The filtrate was concentrated under reduced pressure, and the residue was separated on a silica gel column to obtain a light yellow oil (34.2 g, yield: 76.2%).

$^1$H NMR (400 MHz, CDCl$_3$): 3.15 (s, 1H), 3.39 (t, 2H), 3.53-3.66 (m, 20H), 3.73 (t, 2H).

Methyl 4-{[2,3-difluoro-6-(17-hydroxy-3,6,9,12,15-pentaoxaheptadecan-1-oxy)]benzoyl}benzoate Intermediate (3A) (6.00 g, 20.52 mmol), 17-bromo-3,6,9,12,15-pentaoxaheptadecan-1-ol (21.25 g, 61.56 mmol), K$_2$CO$_3$ (8.51 g, 61.56 mmol) and KI (0.34 g, 2.05 mmol) were dissolved in DMF (125 mL), and the reaction mixture was refluxed overnight under a nitrogen atmosphere. The reaction mixture was cooled to room temperature before distilled water (100 mL) was added, and was extracted with ethyl acetate (3×200 mL). The combined organic layer was washed with saturated brine (300 mL), dried over anhydrous sodium sulfate, and filtered. The filtrate was concentrated under reduced pressure, and the residue was separated on a silica gel column to obtain intermediate (15-06H) as a light yellow solid (7.16 g, yield: 62.7%).

MASS (ESI+) m/z=557 (M+H)$^+$.

Intermediate (16-06H)

4-{[2,3-difluoro-6-(17-hydroxy-3,6,9,12,15-pentaoxaheptadecan-1-oxy)]benzoyl}benzoic acid

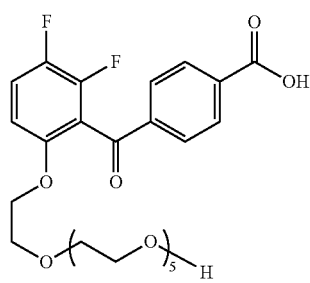

16-06H

Intermediate (15-06H) (7.00 g, 12.58 mmol) was dissolved in tetrahydrofuran (100 mL), and an aqueous solution of 2 N LiOH (40 mL, 20.00 mmol) was added. The reaction mixture was stirred at 50° C. for 4 h, and was then cooled to room temperature. Tetrahydrofuran was distilled off under reduced pressure, and the residue was diluted by adding distilled water (40 mL). The resulting mixture was acidified to pH 3.5 with 1 N HCl, and was extracted with ethyl acetate (3×100 mL). The combined organic layer was washed with brine (100 mL), dried over anhydrous sodium sulfate, and filtered. The filtrate was concentrated under reduced pressure to obtain intermediate (16-06H) as a light yellow solid (5.95 g, yield: 87.2%).

MASS (ESI+) m/z=543 (M+H)$^+$.

Intermediate (17-06H)

Tert-butyl (3R,4R)-3-amino-4-{4-[2,3-difluoro-6-(17-hydroxy-3,6,9,12,15-pentaoxaheptadecan-1-oxy)]benzoyl}benzamidopyrrolidine-1-carboxylate

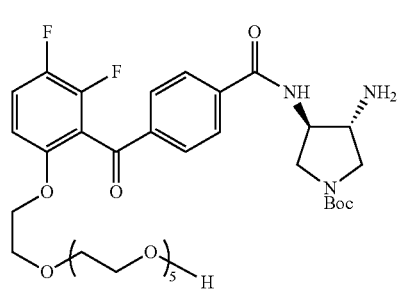

17-06H

HATU (4.57 g, 12.01 mmol) was added to a solution of intermediate (16-06H) (5.92 g, 10.92 mmol), intermediate ((3R,4R)-10) (4.40 g, 21.84 mmol) and DIPEA (2.82 g, 21.84 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (17-06H) as a light yellow solid (4.86 g, yield: 61.3%).

MASS (ESI+) m/z=726 (M+H)$^+$.

Intermediate (18-06H)

Tert-butyl (3R,4R)-3-{4-[2,3-difluoro-6-(17-hydroxy-3,6,9,12,15-pentaoxaheptadecan-1-oxy)]benzoyl}benzamido-4-(1H-indazole-6-carboxamido)pyrrolidine-1-carboxylate

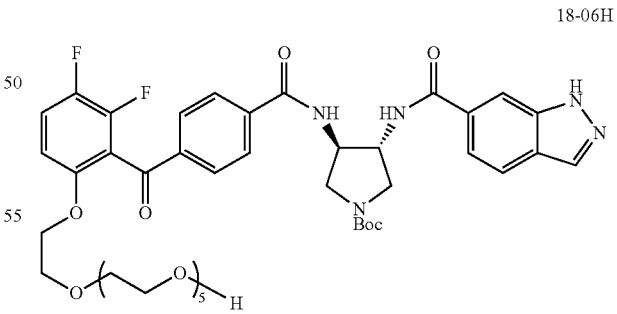

18-06H

HATU (2.67 g, 7.01 mmol) was added to a solution of intermediate (17-06H) (4.62 g, 6.37 mmol), intermediate (13) (1.14 g, 7.01 mmol) and DIPEA (2.47 g, 19.11 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (18-02H) as a light yellow solid (4.53 g, yield: 81.8%).

MASS (ESI+) m/z=870 (M+H)+.

Product (JK-06H)

(3R,4R)-3-{4-[2,3-difluoro-6-(17-hydroxy-3,6,9,12, 15-pentaoxaheptadecan-1-oxy)]benzoyl}benzamido-4-(1H-indazole-6-carboxamido)pyrrolidine hydrochloride

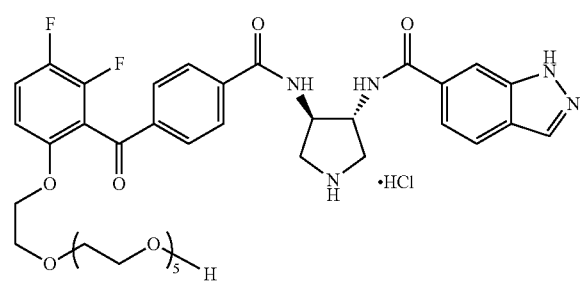

JK-06H

A solution of 4 mol/L hydrogen chloride in ethyl acetate (100 mL) was added to a solution of intermediate (18-06H) (4.50 g, 5.17 mmol) in ethyl acetate (100 mL) which was cooled to 0° C., and the reaction mixture was stirred at room temperature for 2 h. After filtration, the filter cake was washed with ethyl acetate, and dried under vacuum to obtain product (JK-06H) as a light yellow solid (3.32 g, yield: 79.6%).

MASS (ESI+) m/z=770 (M+H)+.

Example 4: The Preparation of (3R,4R)-3-{4-[2,3-difluoro-6-(2,5,8,11,14,17,20-heptaoxadocosan-22-oxy)]benzoyl}benzamido-4-(1H-indazole-6-carboxamido)pyrrolidine hydrochloride (JK-07M)

Intermediate (15-07M)

Methyl 4-{[2,3-difluoro-6-(2,5,8,11,14,17,20-heptaoxadocosan-22-oxy)]benzoyl}benzoate

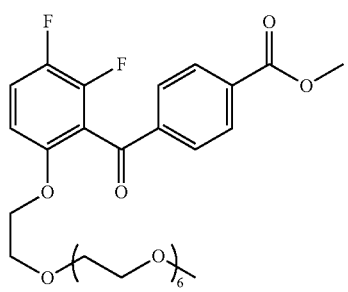

15-07M 22-chloro-2,5,8,11,14,17,20-heptaoxadocosane

Under a nitrogen atmosphere, a solution of thionyl chloride (10.95 g, 92.0 mmol) in CHCl₃ (15 mL) was slowly added dropwise to a solution of heptaethylene glycol monomethyl ether (24.5 g, 72.0 mmol) and pyridine (5.70 g, 72.0 mmol) in CHCl₃ (60 mL). The reaction mixture was stirred under reflux for 3 h. Distilled water (300 mL) was added. After liquid separation, the organic layer was dried over anhydrous sodium sulfate, and concentrated under reduced pressure to obtain a yellow oil (23.6 g, yield: 91.3%), which was used directly in the next reaction without purification.

Methyl 4-{[2,3-difluoro-6-(2,5,8,11,14,17,20-heptaoxadocosan-22-oxy)]benzoyl}benzoate Intermediate (3A) (6.00 g, 20.52 mmol), 22-chloro-2,5, 8,11,14,17,20-heptaoxadocosane (22.09 g, 61.56 mmol), K₂CO₃ (8.51 g, 61.56 mmol) and KI (0.34 g, 2.05 mmol) were dissolved in DMF (125 mL), and the reaction mixture was refluxed overnight under a nitrogen atmosphere. The reaction mixture was cooled to room temperature before distilled water (100 mL) was added, and was extracted with ethyl acetate (100 mL). The combined organic layer was washed with saturated brine (300 mL), dried over anhydrous sodium sulfate, and filtered. The filtrate was concentrated under reduced pressure, and the residue was separated on a silica gel column to obtain intermediate (15-07M) as a light yellow solid (7.45 g, yield: 59.1%).

MASS (ESI+) m/z=615 (M+H)+.

Intermediate (16-07M)

4-{[2,3-difluoro-6-(2,5,8,11,14,17,20-heptaoxadocosan-22-oxy)]benzoyl}benzoic acid

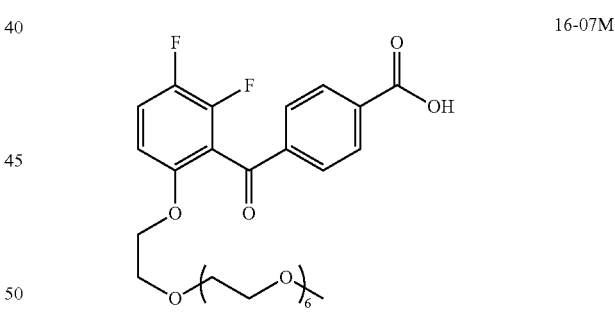

16-07M

Intermediate (15-07M) (7.00 g, 11.39 mmol) was dissolved in tetrahydrofuran (100 mL), and an aqueous solution of 2 N LiOH (36 mL, 18.00 mmol) was added. The reaction mixture was stirred at 50° C. for 4 h, and was then cooled to room temperature. Tetrahydrofuran was distilled off under reduced pressure, and the residue was diluted by adding distilled water (40 mL). The resulting mixture was acidified to pH 3.5 with 1 N HCl, and was extracted with ethyl acetate (3×100 mL). The combined organic layer was washed with brine (100 mL), dried over anhydrous sodium sulfate, and filtered. The filtrate was concentrated under reduced pressure to obtain intermediate (16-07M) as a light yellow solid (6.14 g, yield: 89.8%).

MASS (ESI+) m/z=601 (M+H)+.

Intermediate (17-07M)

Tert-butyl (3R,4R)-3-amino-4-{4-[2,3-difluoro-6-(2,5,8,11,14,17,20-heptaoxadocosan-22-oxy)]benzoyl}benzamidopyrrolidine-1-carboxylate

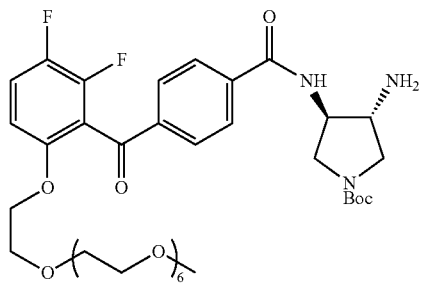

17-07M

HATU (4.57 g, 12.01 mmol) was added to a solution of intermediate (16-07M) (6.56 g, 10.92 mmol), intermediate ((3R,4R)-10) (4.40 g, 21.84 mmol) and DIPEA (2.82 g, 21.84 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (17-07M) as a light yellow solid (5.93 g, yield: 69.3%).

MASS (ESI+) m/z=784 (M+H)$^+$.

Intermediate (18-07M)

Tert-butyl (3R,4R)-3-{4-[2,3-difluoro-6-(2,5,8,11,14,17,20-heptaoxadocosan-22-oxy)]benzoyl}benzamido-4-(1H-indazole-6-carboxamido)pyrrolidine-1-carboxylate

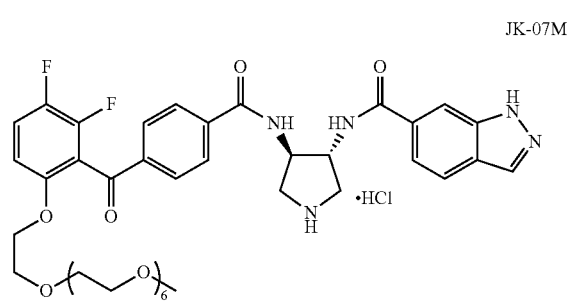

18-07M

HATU (2.67 g, 7.01 mmol) was added to a solution of intermediate (17-07M) (4.99 g, 6.37 mmol), intermediate (13) (1.14 g, 7.01 mmol) and DIPEA (2.47 g, 19.11 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (18-07M) as a light yellow solid (5.17 g, yield: 87.4%).

MASS (ESI+) m/z=928 (M+H)$^+$.

Product (JK-07M)

(3R,4R)-3-{4-[2,3-difluoro-6-(2,5,8,11,14,17,20-heptaoxadocosan-22-oxy)]benzoyl}benzamido-4-(1H-indazole-6-carboxamido)pyrrolidine hydrochloride

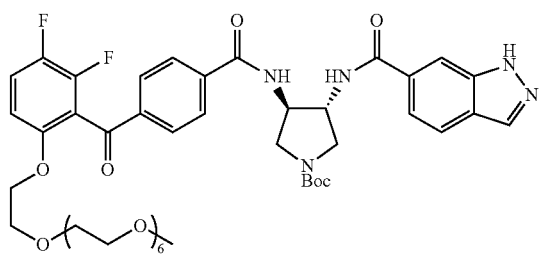

JK-07M

A solution of 4 mol/L hydrogen chloride in ethyl acetate (100 mL) was added to a solution of intermediate (18-07M) (4.69 g, 5.05 mmol) in ethyl acetate (100 mL) which was cooled to 0° C., and the reaction mixture was stirred at room temperature for 2 h. After filtration, the filter cake was washed with ethyl acetate, and dried under vacuum to obtain product (JK-07M) as a light yellow solid (3.61 g, yield: 82.7%).

MASS (ESI+) m/z=828 (M+H)$^+$.

Example 5: The Preparation of (3R,4R)-3-{4-[2,3-difluoro-6-(4,7-dioxanonan-9-oxy)]benzoyl}benzamido-4-(1H-indazole-6-carboxamido)pyrrolidine hydrochloride (JK-02P)

Intermediate (15-02P)

Methyl 4-{[2,3-difluoro-6-(3,6-dioxanonan-1-oxy)]benzoyl}benzoate

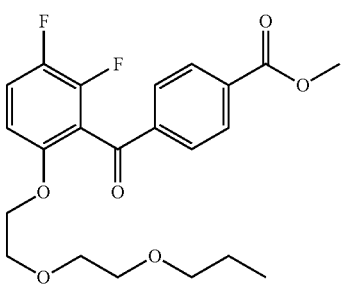

15-02P 3,6-dioxanonan-1-ol

Under cooling in an ice-water bath, NaH (60%, 25.0 g, 0.63 mol) was added to a solution of diethylene glycol (424.5 g, 4.0 mol) in tetrahydrofuran (2.5 L), and then 1-bromopropane (24.6 g, 0.20 mol) was added dropwise. The reaction mixture was refluxed for 12 h. The solvent was distilled off under reduced pressure. Distilled water (2.5 L) was added to the residue, and the resulting mixture was extracted with ethyl acetate (3×2.0 L). The combined organic layer was dried over anhydrous sodium sulfate, and the solvent was distilled off under reduced pressure to obtain a colorless oil (23.2 g, yield: 78.3%). The product was used directly in the next reaction without purification.

3,6-dioxanonyl-1-p-toluenesulfonate

Under cooling with an ice-salt bath, a solution of p-toluenesulfonyl chloride (85.7 g, 0.45 mol) in dichloromethane (125 mL) was added dropwise to a mixed solution of 3,6-dioxanonan-1-ol (44.5 g, 0.30 mol) and pyridine (35.5 g, 0.45 mol), with the rate of addition controlled so that the temperature of the reaction solution was kept lower than 20° C. The reaction solution was stirred overnight at room temperature. Distilled water (100 mL) was added, and the pH of the reaction mixture was adjusted to 4.0 with a 6 N NaOH solution. After liquid separation, the organic layer was washed with distilled water (2×50 mL). Distilled water (100 mL) was added to the organic layer, and the pH was adjusted to 1.5 with a solution of 6 N HCl. After liquid separation, the organic layer was washed with distilled water (2×50 mL). The organic layer was dried over anhydrous sodium sulfate and filtered. The solvent was distilled off under reduced pressure to obtain a light yellow oil (61.5 g, yield: 67.8%).

$^1$H NMR (400 MHz, CDCl$_3$): 0.93 (s, 3H), 1.59 (m, 2H), 2.45 (s, 3H), 3.45 (m, 2H), 3.51 (t, 2H), 3.57 (m, 2H), 3.67-3.73 (m, 2H), 4.16 (t, 2H), 7.34 (d, 2H), 7.80 (d, 2H).

1-bromo-3,6-dioxanonane

Under cooling with an ice-salt bath, lithium bromide (16.3 g, 0.19 mol) was slowly added to a solution of 3,6-dioxanonyl-1-p-toluenesulfonate (39.3 g, 0.13 mol) in DMF (40 mL), with the rate of addition controlled so that the temperature of the reaction solution was kept lower than 20° C.

The reaction solution was vigorously stirred overnight at room temperature. Ethyl acetate (125 mL) was added, and the reaction solution was stirred for 1 h before filtration. The filtrate was washed with distilled water (2×100 mL). The organic layer was dried over anhydrous sodium sulfate and filtered. The filtrate was concentrated under reduced pressure, and the residue was separated on a silica gel column to obtain a colorless oil (24.3 g, yield: 88.5%).

$^1$H NMR (400 MHz, CDCl$_3$): 0.92 (t, 3H), 1.61 (m, 2H), 3.43 (m, 2H), 3.47 (m, 2H), 3.59 (m, 2H), 3.67 (m, 2H), 3.82 (t, 2H).

Methyl 4-{[2,3-difluoro-6-(3,6-dioxanonan-1-oxy)]benzoyl}benzoate

Intermediate (3A) (6.00 g, 20.52 mmol), 1-bromo-3,6-dioxanonane (13.00 g, 61.56 mmol), K$_2$CO$_3$ (8.51 g, 61.56 mmol) and KI (0.34 g, 2.05 mmol) were dissolved in DMF (125 mL), and the reaction mixture was refluxed overnight under a nitrogen atmosphere. The reaction mixture was cooled to room temperature before distilled water (100 mL) was added, and was extracted with ethyl acetate (3×200 mL). The combined organic layer was washed with saturated brine (300 mL), dried over anhydrous sodium sulfate, and filtered. The filtrate was concentrated under reduced pressure, and the residue was separated on a silica gel column to obtain intermediate (15-02P) as a light yellow solid (5.92 g, yield: 68.3%).

MASS (ESI+) m/z=423 (M+H)$^+$.

Intermediate (16-02P)

4-{[2,3-difluoro-6-(3,6-dioxanonan-1-oxy)]benzoyl}benzoic acid

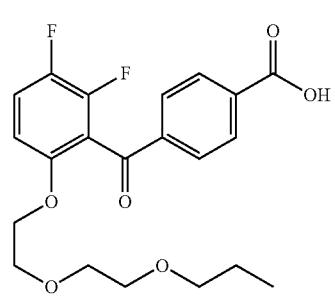

16-02P

Intermediate (15-02P) (5.00 g, 11.84 mmol) was dissolved in tetrahydrofuran (100 mL), and an aqueous solution of 2 N LiOH (38 mL, 19.00 mmol) was added. The reaction mixture was stirred at 50° C. for 4 h, and was then cooled to room temperature. Tetrahydrofuran was distilled off under reduced pressure, and the residue was diluted by adding distilled water (40 mL). The resulting mixture was acidified to pH 3.5 with 1 N HCl, and was extracted with ethyl acetate (3×100 mL). The combined organic layer was washed with brine (100 mL), dried over anhydrous sodium sulfate, and filtered. The filtrate was concentrated under reduced pressure to obtain intermediate (16-02P) as a light yellow solid (4.49 g, yield: 92.8%).

MASS (ESI+) m/z=409 (M+H)$^+$.

Intermediate (17-02P)

Tert-butyl (3R,4R)-3-amino-4-{4-[2,3-difluoro-6-(3,6-dioxanonan-1-oxy)]benzoyl}benzamidopyrrolidine-1-carboxylate

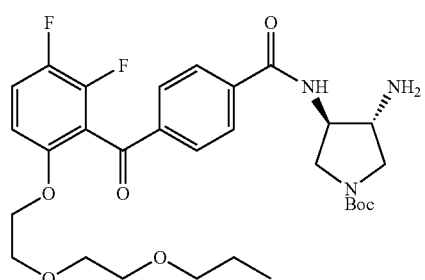

17-02P

HATU (4.57 g, 12.01 mmol) was added to a solution of intermediate (16-02P) (4.46 g, 10.92 mmol), intermediate ((3R,4R)-10) (4.40 g, 21.84 mmol) and DIPEA (2.82 g, 21.84 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (17-02P) as a light yellow solid (4.76 g, yield: 73.7%).

MASS (ESI+) m/z=592 (M+H)⁺.

Intermediate (18-02P)

Tert-butyl (3R,4R)-3-{4-[2,3-difluoro-6-(3,6-dioxanonan-1-oxy)]benzoyl}benzamido-4-(1H-indazole-6-carboxamido)pyrrolidine-1-carboxylate

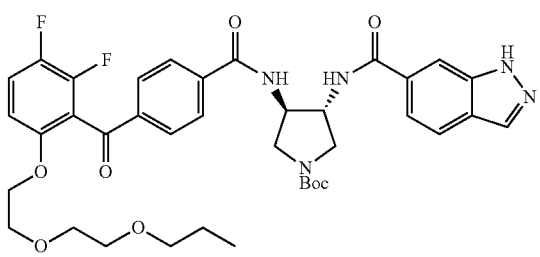

18-02P

HATU (2.67 g, 7.01 mmol) was added to a solution of intermediate (17-02P) (3.77 g, 6.37 mmol), intermediate (13) (1.14 g, 7.01 mmol) and DIPEA (2.47 g, 19.11 mmol) in DMF (50 mL) which was cooled to 0° C. The reaction mixture was stirred overnight at room temperature before distilled water (100 mL) was added, and was extracted with ethyl acetate (3×100 mL). The combined organic layer was washed with saturated brine (150 mL), dried over anhydrous sodium sulfate, and filtered. The filtrate was concentrated under reduced pressure, and the residue was separated on a silica gel column to obtain intermediate (18-02H) as a light yellow solid (4.13 g, yield: 88.1%).

MASS (ESI+) m/z=736 (M+H)⁺.

Product (JK-02P)

(3R,4R)-3-{4-[2,3-difluoro-6-(3,6-dioxanonan-1-oxy)]benzoyl}benzamido-4-(1H-indazole-6-carboxamido)pyrrolidine hydrochloride

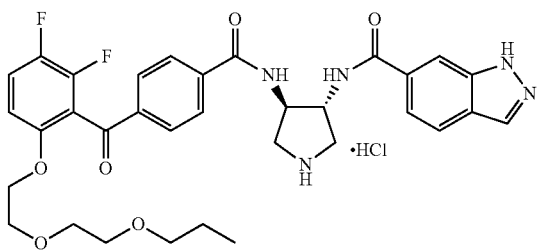

JK-02P

A solution of 4 mol/L hydrogen chloride in ethyl acetate (100 mL) was added to a solution of intermediate (18-02P) (3.50 g, 4.76 mmol) in ethyl acetate (100 mL) which was cooled to 0° C., and the reaction mixture was stirred at room temperature for 2 h. After filtration, the filter cake was washed with ethyl acetate, and dried under vacuum to obtain product (JK-02H) as a light yellow solid (2.86 g, yield: 89.4%).

MASS (ESI+) m/z=636 (M+H)⁺.

Example 6: The Preparation of (3R,4R)-3-{4-[2-fluoro-3-methoxy-6-(5-hydroxy-3-oxapentan-1-oxy)]benzoyl}benzamido-4-(1H-indazole-6-carboxamido)pyrrolidine hydrochloride (JK-M02H)

Intermediate (1B)

Methyl 4-[(2-fluoro-3-methoxy-6-benzyloxyphenyl)hydroxymethyl]benzoate

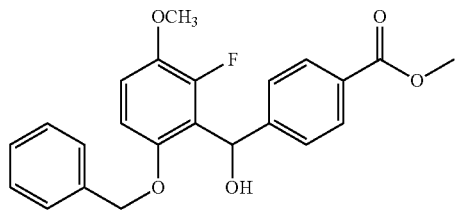

1B 1-methoxy-2-fluoro-4-benzyloxybenzene 3-fluoro-4-methoxyphenol (7.5 g, 52.8 mmol) and cesium carbonate (34.5 g, 105.8 mmol) were dissolved in acetonitrile (400 mL), and benzyl bromide (18.1 g, 105.8 mmol) was slowly added dropwise with stirring. The reaction mixture was stirred under reflux for 5 h, and was concentrated under reduced pressure. The residue was dissolved in diethyl ether (2.0 L), and was washed by adding distilled water (3×300 mL). The organic layer was dried over anhydrous sodium sulfate, and concentrated under reduced pressure. The residue was separated on a silica gel column to obtain a light yellow oil (10.8 g, yield: 88.1%).

MASS (ESI+) m/z=233 (M+H)⁺.

¹H NMR (400 MHz, CDCl₃): 3.76 (s, 3H), 5.01 (s, 2H), 6.83 (d, 1H), 6.91 (d, 1H), 7.03 (s, 1H), 7.31 (m, 1H), 7.37 (m, 2H), 7.42 (m, 2H).

Methyl 4-[(2-fluoro-3-methoxy-6-benzyloxyphenyl)hydroxymethyl]benzoate

The title compound was synthesized according to the method of Example 1, using 1-methoxy-2-fluoro-4-benzyloxybenzene to replace 3,4-difluoroanisole as a starting material.

MASS (ESI+) m/z=397 (M+H)+.

¹H NMR (400 MHz, CDCl₃): 3.76 (s, 3H), 3.88 (s, 3H), 4.29 (d, 1H), 5.01 (s, 2H), 6.36 (d, 1H), 6.83 (d, 1H), 6.91 (d, 1H), 7.31 (m, 1H), 7.37 (m, 2H), 7.42 (m, 2H), 7.47 (d, 2H), 7.95 (d, 2H).

Intermediate (2B)

Methyl 4-[(2-fluoro-3-methoxy-6-benzyloxy)benzoyl]benzoate

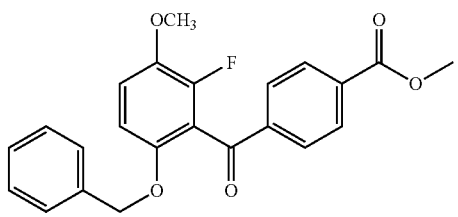

2B

The title compound was synthesized according to the method of Example 1, using intermediate (1B) to replace intermediate (1A) as a starting material.

MASS (ESI+) m/z=395 (M+H)+.

¹H NMR (400 MHz, CDCl₃): 3.76 (s, 3H), 3.94 (s, 3H), 5.01 (s, 2H), 6.93 (d, 1H), 7.27 (d, 1H), 7.31 (m, 1H), 7.37 (m, 2H), 7.42 (m, 2H), 7.82 (d, 2H), 8.09 (d, 2H).

Intermediate (3B)

Methyl 4-[(2-fluoro-3-methoxy-6-hydroxy)benzoyl]benzoate

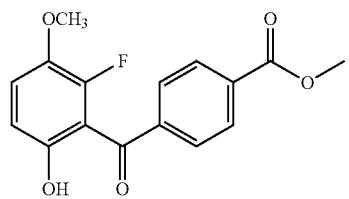

3B

Intermediate (2B) (15.0 g, 38.0 mmol) and 20% Pd(OH)₂/C (3.0 g) were dissolved in THF-MeOH (1:1, 250 mL). Hydrogen was supplied to replace the air for three times, and the reaction was kept for 4 h under a hydrogen atmosphere. The reaction mixture was filtered, and the filtrate was concentrated under reduced pressure. The residue was separated on a silica gel column to obtain intermediate (3B) as a light yellow solid (10.6 g, yield: 91.7%).

MASS (ESI+) m/z=305 (M+H)+.

¹H NMR (400 MHz, CDCl₃): 3.78 (s, 3H), 3.98 (s, 3H), 6.89 (d, 1H), 7.25 (d, 1H), 7.74 (d, 2H), 8.17 (d, 2H), 11.30 (s, 1H).

Product (JK-M02H)

(3R,4R)-3-{4-[2-fluoro-3-methoxy-6-(5-hydroxy-3-oxapentan-1-oxy)]benzoyl}benzamido-4-(1H-indazole-6-carboxamido)pyrrolidine hydrochloride

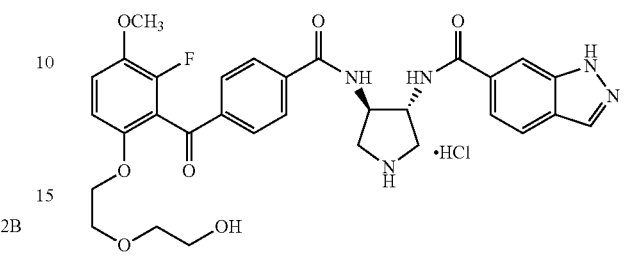

JK-M02H

The title compound was synthesized according to the method of Example 1, using intermediate (3B) to replace intermediate (3A) as a starting material.

MASS (ESI+) m/z=606 (M+H)+.

Example 7: The Preparation of (3R,4R)-3-{4-[2-fluoro-3-methoxy-6-(2,5,8-trioxadecan-10-oxy)]benzoyl}benzamido-4-(1H-indazole-6-carboxamido)pyrrolidine hydrochloride (JK-M03M)

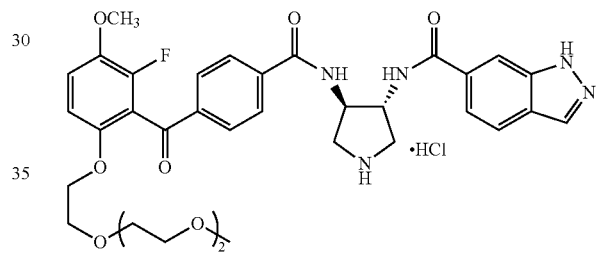

JK-M03M

The title compound was synthesized according to the method of Example 2, using intermediate (3B) to replace intermediate (3A) as a starting material.

MASS (ESI+) m/z=664 (M+H)+.

Example 8: The Preparation of (3R,4R)-3-{4-[2-fluoro-3-methoxy-6-(17-hydroxy-3,6,9,12,15-pentaoxaheptadecan-1-oxy)]benzoyl}benzamido-4-(1H-indazole-6-carboxamido)pyrrolidine hydrochloride (JK-M06H)

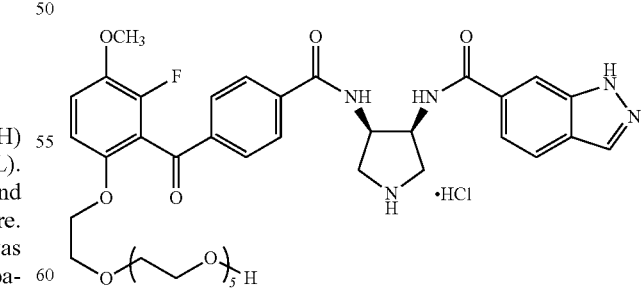

JK-M06H

The title compound was synthesized according to the method of Example 3, using intermediate (3B) to replace intermediate (3A) as a starting material.

MASS (ESI+) m/z=782 (M+H)+.

Example 9: The Preparation of (3R,4R)-3{4-[2-fluoro-3-methoxy-6-(2,5,8,11,14,17,20-heptaoxadocosan-22-oxy)]benzoyl}benzamido-4-(1H-indazole-6-carboxamido)pyrrolidine hydrochloride (JK-M07M)

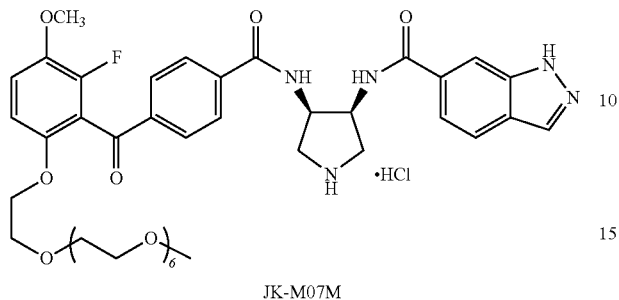

JK-M07M

The title compound was synthesized according to the method of Example 4, using intermediate (3B) to replace intermediate (3A) as a starting material.
MASS (ESI+) m/z=840 (M+H)$^+$.

Example 10: The Preparation of (3R,4R)-3-{4-[2-fluoro-3-methoxy-6-(4,7-dioxanonan-9-oxy)]benzoyl}benzamido-4-(1H-indazole-6-carboxamido)pyrrolidine hydrochloride (JK-M02P)

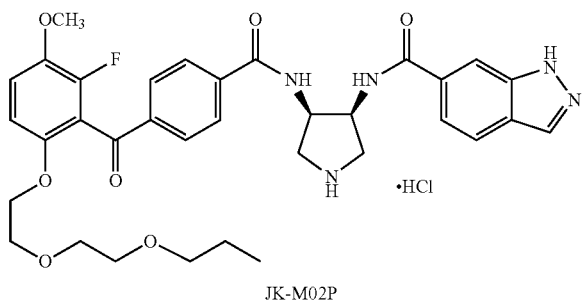 [SMILES: CCCOCCOCCOc1ccc(OC)c(F)c1C(=O)c1ccc(C(=O)N[C@@H]2CNC[C@@H]2NC(=O)c2ccc3cn[nH]c3c2)cc1 ; Cl]

JK-M02P

The title compound was synthesized according to the method of Example 5, using intermediate (3B) to replace intermediate (3A) as a starting material.
MASS (ESI+) m/z=648 (M+H)$^+$.

Example 11: The Preparation of (3R,4R)-3-{4-[2,3-dimethoxy-6-(17-hydroxy-3,6,9,12,15-pentaoxaheptadecan-1-oxy)]benzoyl}benzamido-4-(1H-indazole-6-carboxamido)pyrrolidine hydrochloride (JK-WO6H)

Intermediate (3C)

Methyl 4-[(2,3-dimethoxy-6-hydroxy)benzoyl]benzoate

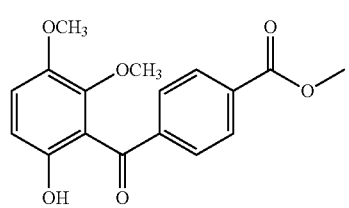

3C

The title compound was synthesized according to the method of Example 6, using 3,4-dimethoxyphenol to replace 3-fluoro-4-methoxyphenol as a starting material.
MASS (ESI+) m/z=317 (M+H)$^+$.
$^1$H NMR (400 MHz, CDCl$_3$): 3.79 (s, 6H), 3.98 (s, 3H), 6.36 (d, 1H), 6.72 (d, 1H), 7.74 (d, 2H), 8.17 (d, 2H), 11.29 (s, 1H).

Product (JK-MM06H)

(3R,4R)-3-{4-[2,3-dimethoxy-6-(17-hydroxy-3,6,9,12,15-pentaoxaheptadecan-1-oxy)]benzoyl}benzamido-4-(1H-indazole-6-carboxamido)pyrrolidine hydrochloride

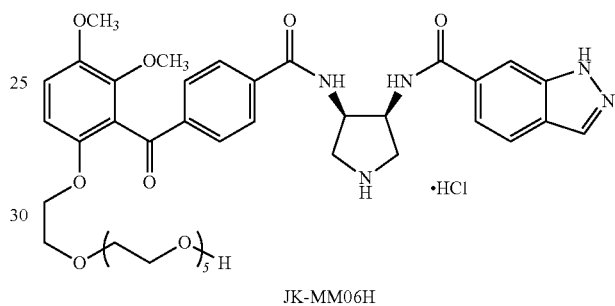

JK-MM06H

The title compound was synthesized according to the method of Example 3, using intermediate (3C) to replace intermediate (3A) as a starting material.
MASS (ESI+) m/z=794 (M+H)$^+$.

Example 12: The Preparation of (3R,4R)-3-{4-[2,3-dimethoxy-6-(5-hydroxy-3-oxapentan-1-oxy)]benzoyl}benzamido-4-(1H-indazole-6-carboxamido)pyrrolidine hydrochloride (JK-MN02H)

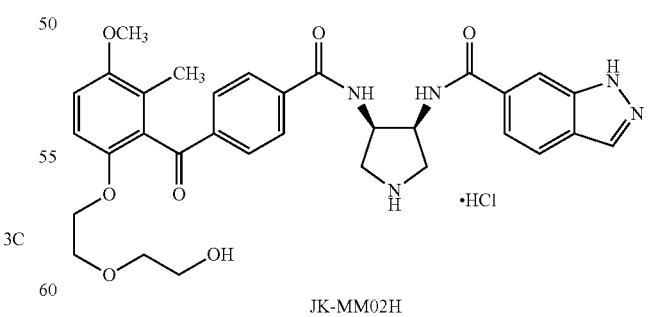

JK-MM02H

The title compound was synthesized according to the method of Example 1, using intermediate (3C) to replace intermediate (3A) as a starting material.
MASS (ESI+) m/z=602 (M+H)$^+$.

Example 13: The Preparation of (3R,4R)-3-{4-[2-fluoro-3-ethenyl-6-(2,5,8-trioxadecan-10-oxy)]benzoyl}benzamido-4-(1H-indazole-6-carboxamido)pyrrolidine hydrochloride (JK-E03M)

Intermediate (3D)

Methyl 4-[(2-fluoro-3-ethenyl-6-hydroxy)benzoyl]benzoate

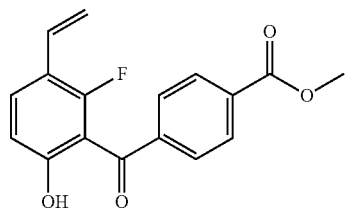

2-Fluoro-4-methoxystyrene n-Butyl lithium (a 2.5 M solution in tetrahydrofuran, 40 mL) was added dropwise to a solution of methyl triphenyl phosphonium bromide (35.7 g, 0.10 mol) in tetrahydrofuran (850 mL). After the addition, the mixture was stirred for 15 min to obtain a yellow solution. 2-Fluoro-4-methoxybenzaldehyde (15.4 g, 0.10 mol) was added in portions, with the color of the solution becoming lighter gradually. After the addition, the solution was further stirred for 2 h. A saturated ammonium chloride solution was added, and the reaction mixture was extracted with dichloromethane. The organic phase was dried over anhydrous sodium sulfate, filtered, and concentrated under reduced pressure. The residue was separated on a silica gel column to obtain a light yellow oil (11.8 g, yield: 77.5%).

MASS (ESI+) m/z=153 (M+H)$^+$.

$^1$H NMR (400 MHz, CDCl$_3$): 3.79 (s, 3H), 5.24 (dd, 1H), 5.58 (dd, 1H), 6.84 (dd, 1H), 6.98 (dd, 1H), 7.09 (d, 1H), 7.47 (d, 1H).

Methyl 4-[(2-fluoro-3-ethenyl-6-hydroxy)benzoyl]benzoate

The title compound was synthesized according to the method of Example 1, using 2-fluoro-4-methoxystyrene to replace 3,4-difluoroanisole as a starting material.

MASS (ESI+) m/z=301 (M+H)$^+$.

$^1$H NMR (400 MHz, CDCl$_3$): 3.98 (s, 3H), 5.24 (dd, 1H), 5.58 (dd, 1H), 6.78 (d, 1H), 6.98 (dd, 1H), 7.40 (d, 1H), 7.73 (d, 2H), 8.15 (d, 2H), 11.29 (s, 1H).

Product (JK-E03M)

(3R,4R)-3-{4-[2-fluoro-3-ethenyl-6-(2,5,8-trioxadecan-10-oxy)]benzoyl}benzamido-4-(1H-indazole-6-carboxamido)pyrrolidine hydrochloride (JK-E03M)

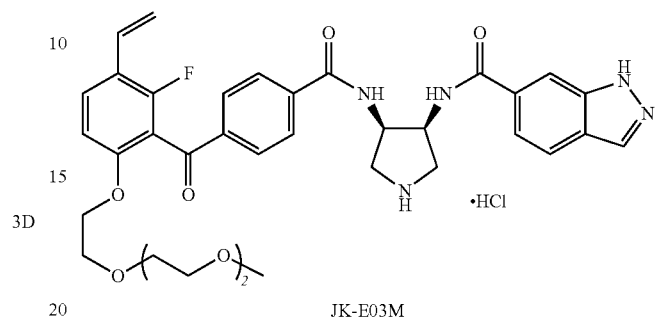

The title compound was synthesized according to the method of Example 2, using intermediate (3D) to replace intermediate (3A) as a starting material.

MASS (ESI+) m/z=660 (M+H)$^+$.

Example 14: The Preparation of (3R,4R)-3-{4-[2-fluoro-3-propynyl-6-(2,5,8-trioxadecan-10-oxy)]benzoyl}benzamido-4-(1H-indazole-6-carboxamido)pyrrolidine hydrochloride (JK-PM06H)

Intermediate (3E)

Methyl 4-{[2-methyl-3-(1-propynyl)-6-hydroxy]benzoyl}benzoate

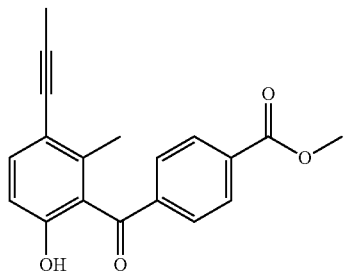

2-Methyl-4-methoxyiodobenzene m-Methylanisole (24.4 g, 0.20 mol) was dissolved in acetonitrile (800 mL), and N-iodosuccinimide (67.5 g, 0.30 mol) was added. The reaction mixture was warmed to 82° C., and was kept at this temperature for 2 h under stirring. The solvent was distilled off under reduced pressure, and diethyl ether (800 mL) was added. The resulting mixture was successively washed with an aqueous solution of sodium bisulfite and distilled water. The organic phase was dried over anhydrous sodium sulfate, filtered, and concentrated under reduced pressure. The residue was separated on a silica gel column to obtain a light yellow oil (43.2 g, yield: 87.1%).

MASS (ESI+) m/z=249 (M+H)$^+$.

$^1$H NMR (400 MHz, CDCl$_3$): 2.39 (s, 3H), 3.77 (s, 3H), 6.47 (dd, 1H), 6.81 (d, 1H), 7.65 (d, 1H).

1-(2-Methyl-4-methoxy)phenyl-1-propyne 2-methyl-4-methoxyiodobenzene (24.8 g, 0.10 mol), 2-butynoic acid (11.7 g, 0.14 mol), cuprous iodide (0.38 g, 2.0 mmol), triphenylphosphine (1.05 g, 4.0 mmol) and potassium carbonate (41.5 g, 0.30 mol) were dissolved in dimethyl sulfoxide (1.0 L), and nitrogen was supplied. The reaction mixture was warmed to 100° C., and was kept at this temperature for 24 h under stirring. The reaction mixture was cooled to room temperature, diluted with distilled water (3.0 L), and extracted with ethyl acetate (3×1.0 L). The organic phase was dried over anhydrous sodium sulfate, filtered, and concentrated under reduced pressure. The residue was separated on a silica gel column to obtain a light yellow oil (13.1 g, yield: 81.8%).

MASS (ESI+) m/z=161 (M+H)$^+$.

$^1$H NMR (400 MHz, CDCl$_3$): 2.05 (s, 3H), 2.34 (s, 3H), 3.82 (s, 3H), 6.84 (dd, 1H), 6.98 (d, 1H), 7.35 (d, 1H).

Methyl 4-{[2-methyl-3-(1-propynyl)-6-hydroxy]benzoyl}benzoate

The title compound was synthesized according to the method of Example 1, using 1-(2-methyl-4-methoxy)phenyl-1-propyne to replace 3,4-difluoroanisole as a starting material.

MASS (ESI+) m/z=309 (M+H)$^+$.

$^1$H NMR (400 MHz, CDCl$_3$): 2.05 (s, 3H), 2.34 (s, 3H), 3.98 (s, 3H), 6.78 (d, 1H), 7.40 (d, 1H), 7.73 (d, 2H), 8.15 (d, 2H), 11.30 (s, 1H).

Product (JK-PM06H)

(3R,4R)-3-{4-[2-methyl-3-(1-propynyl)-6-(17-hydroxy-3,6,9,12,15-pentaoxaheptadecan-1-oxy)]benzoyl}benzamido-4-(1H-indazole-6-carboxamido)pyrrolidine hydrochloride

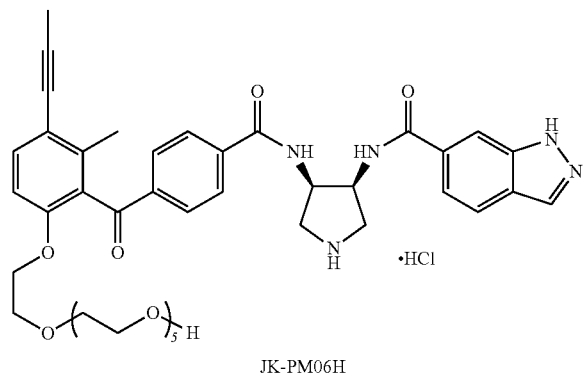

JK-PM06H

The title compound was synthesized according to the method of Example 3, using intermediate (3E) to replace intermediate (3A) as a starting material.

MASS (ESI+) m/z=786 (M+H)$^+$.

Example 15: Test of Water Solubility of the Compounds

At room temperature, about 0.1 g of each sample to be tested (solid materials should be ground as powder) was added to a 10 mL cylinder with a ground glass stopper. Water was gradually added. After each addition of 0.5 mL water, the resulting solution was stirred for 10 min for mixing, and was then visually examined for the presence of any undissolved sample. If there still exists undissolved sample or undissolved portions of the sample after 10 mL water was added, the test would be continued in a 100 mL cylinder. The solubility of each compound at room temperature is shown in Table 1:

TABLE 1

Solubility of tested compounds

| | No. | | | | | | |
|---|---|---|---|---|---|---|---|
| | 46 | JK-02A | JK-02H | JK-03M | JK-06H | JK-07M | JK-02P |
| Volume of added water (mL) | 66.5 | 71.5 | 13.5 | 16.5 | 6.5 | 8.5 | 22.5 |
| Solubility (mg/mL) | 1.5 | 1.4 | 7.4 | 6.1 | 15.4 | 11.8 | 4.4 |

| | No. | | | | |
|---|---|---|---|---|---|
| | JK-M02H | JK-M03M | JK-M06H | JK-M07M | JK-M02P |
| Volume of added water (mL) | 12.5 | 16.0 | 6.0 | 7.5 | 22.0 |
| Solubility (mg/mL) | 8.0 | 6.3 | 16.7 | 13.3 | 4.5 |

As can be seen from the data listed in Table 1, compared with the parent compound, the compounds incorporated with a low-molecule polyethylene glycol fragment have much higher water solubility. Particularly, the solubility of some compounds is almost 10 times higher than the parent compound.

Example 16: Study of the Therapeutic Effect of Compounds JK-02H, 46 and JK-02A on Hyperalgesia Induced by Freund's Complete Adjuvant (CFA) in Rats 1. Design of Study Compounds 46 and JK-02A were prepared according to the disclosure of US patent application No. US2008/0176920, and compound JK-02H was prepared according to Example 1. A repeat efficacy study was carried out on the same batch of animals with a single-dose treatment followed by a washing-out period. The 14 days in life studies included two stages: a single low dose treatment assessment on the 7$^{th}$ day and then a single high dose treatment test on the 14$^{th}$ day after CFA injection.

1.1 Animals
1.1.1 Species: SD rats
1.1.2 Supplier: Beijing Vital River Co. Ltd.
1.1.3 Total number: 40, with 8 rats used for maximal tolerance dose (MTD) test, and 32 used for efficacy study.
1.1.4 Gender: Female
1.1.5 Age: 5-7 weeks, 6-8 weeks after a 7-day acclimation period
1.1.6 Body weight: 150-170 g, 180-200 g when study began.
1.2 Groups and Treatments
On the 7$^{th}$ day after CFA injection, the rats were randomly assigned to respective groups using a computer generated randomization procedure based on the body weight and the baseline values of Von Frey and weight bearing test. Animals received corresponding single dose treatments (vehicle and 3 test articles) on the 7$^{th}$ and 14$^{th}$ days after CFA injection, respectively, and the effect of the test compounds were evaluated. Hyperalgesia of all the study animals was assessed following a single low dose treatment with the test articles on day 7, while a single high dose effect of the test article was evaluated on day 14. The study groups, number of animals per group and treatment paradigms are shown in Table 2.

TABLE 2

Groups and treatments

| Group | Treatment | 1$^{st}$ dose on day 7 (mg/kg) | 2$^{nd}$ dose on day 14 (mg/kg) | Route | Number of animals |
|---|---|---|---|---|---|
| 1 | CFA + Vehicle | — | — | i.v. | 8 |
| 2 | CFA + 46 | 10 | 40 | i.v. | 8 |
| 3 | CFA + JK-02A | 10 | 40 | i.v. | 8 |
| 4 | CFA + JK-02H | 5 | 20 | i.v. | 8 |

1.3 CFA Injection Procedure
1.3.1 Agent: 4 mg/kg CFA
1.3.2 Route: Left hind paw plantar injection
1.3.3 Volume: 50 μL per animal
1.3.4 Frequency: single injection at 9:00 a.m. on day 0.
1.4 Dosing Procedure
1.4.1 Vehicle: 10% hydroxypropyl β cyclodextrin
1.4.1.1 Route: intravenous injection
1.4.1.2 Volume: 4 mL/kg
1.4.1.3 Frequency: single dose at 9:00 a.m. on day 7 and day 14, respectively
1.4.1.4 Formulation: 1.0 g hydroxypropyl β cyclodextrin was dissolved in 5 mL physiological saline, and the resulting solution was subjected to vortexing and sonification until a uniform solution was achieved. Then physiological saline was added into the resulting solution to make up the volume to 10 mL. Finally, the solution was filtered through a 0.22 μm filter membrane. All the processes should be carried on at a cleaning bench.
1.4.2 Test article: compound 46
1.4.2.1 Route: intravenous injection
1.4.2.2 Volume: 4 mL/kg
1.4.2.3 Frequency: single dose at 9:00 a.m. on day 7 and day 14, respectively
1.4.2.4 Formulation: 25.0 mg compound 46 was dissolved in 5 mL physiological saline containing 20% hydroxypropyl β cyclodextrin, and the resulting solution was subjected to vortexing and sonification until a uniform solution was achieved. Then physiological saline was added into the resulting solution to make up the volume to 10 mL. The final concentration of the solution was 2.5 mg/mL (10 mg/kg). Finally, the solution was filtered through a 0.22 μm filter membrane. All the processes were carried on at a cleaning bench.
1.4.3 Test article: compound JK-02A
1.4.3.1 Route: intravenous injection
1.4.3.2 Volume: 4 mL/kg
1.4.3.3 Frequency: single dose at 9:00 a.m. on day 7 and day 14, respectively
1.4.3.4 Formulation: 25.0 mg compound JK-02A was dissolved into 5 mL physiological saline containing 20% hydroxypropyl β cyclodextrin, and the resulting solution was subjected to vortexing and sonification, until a uniform solution was achieved. Then physiological saline was added into the resulting solution to make up the volume to 10 mL. The final concentration of the solution was 2.5 mg/mL (10 mg/kg). Finally, the solution was filtered through a 0.22 μm filter membrane. All the processes were carried on at a cleaning bench.
1.4.4 Test article: compound JK-02H
1.4.4.1 Route: intravenous injection
1.4.4.2 Volume: 4 mL/kg
1.4.4.3 Frequency: single dose at 9:00 a.m. on day 7 and day 14, respectively
1.4.4.4 Formulation: 12.5 mg compound JK-02H was dissolved in 5 mL physiological saline containing 20% hydroxypropyl β cyclodextrin, and the resulting solution was subjected to vortexing and sonification until a uniform solution was achieved. Then physiological saline was added into the resulting solution to make up the volume to 10 mL. The final concentration of the solution was 1.25 mg/mL (5 mg/kg). Finally, the solution was filtered through a 0.22 μm filter membrane. All the processes were carried on at a cleaning bench.

TABLE 3

Dosing Paradigm

| Formulation | Concentration on day 7 (mg/mL) | Concentration on day 14 (mg/mL) | Route | Volume (mL/kg) |
|---|---|---|---|---|
| Vehicle | — | — | i.v. | 4 |
| 46 | 2.5 | 10 | i.v. | 4 |
| JK-02A | 2.5 | 10 | i.v. | 4 |
| JK-02H | 1.25 | 5 | i.v. | 4 |

2. Measurement Parameters and Assay Protocol

The mechanical hyperalgesia and weight bearing were measured on day 7 and day 14 after CFA injection, followed by administration of control or test articles. Von Frey filaments and weight bearing were measured on all the study animals at three time points on day 7, and four time points on day 14. An extra time point assessment was conducted on day 14, considering the strong analgesic effect of the test articles at a higher dose noticed during the test at the 3$^{th}$ time point.

2.1 Von Frey Filament Test

Mechanical hyperalgesia of the left hind paw was measured before and during the course of study in all animal groups by determining withdrawal thresholds to Von Frey filament (Bioseb, France). Increasing tensile force perpendicular to the plantar surface of the paw was applied to the filaments. The threshold for paw withdrawal was calculated by taking the average of 2-3 repeated stimuli (unit in "g").

On day 7, Von Frey Filament measurements were conducted three times, at the time points of pretreatment, 15 min and 2 hours post treatment. Following a one-week washing out period, on day 14 after CFA injection, Von Frey Filament tests were performed again four times post a single high dose administration. Rats treated with vehicle or high dose test articles were measured at the time points of pretreatment, 15 min, 2 and 5 hours post treatment.

2.2 Weight Bearing Test

Rats distributed body weight unequally on the CFA-injected and contra lateral paws, which was measured by a weight balance changing instrument (Bio-medical, USA).

The animals were tested in a box constructed to register the weight load exerted by the hind paws by means of force plates inserted in the floor. The mean weight bearing (unit in "g") between the CFA-injected paw and the contra-lateral paw was determined in 10 seconds. The weight bearing test of all study animals was conducted at the same time intervals as the mechanical hyperalgesia test.

2.3 Statistic Analysis

All the results were expressed as mean±SD. One-way analysis of variance (ANOVA) followed by a multiple comparison test were applied among the groups, $p<0.05$ accepted as significant.

3. Study Results

The Von Frey and weight bearing's baselines of individual animal are listed in Table 8.

3.1 Von Frey Filament Test

Figure 1B:
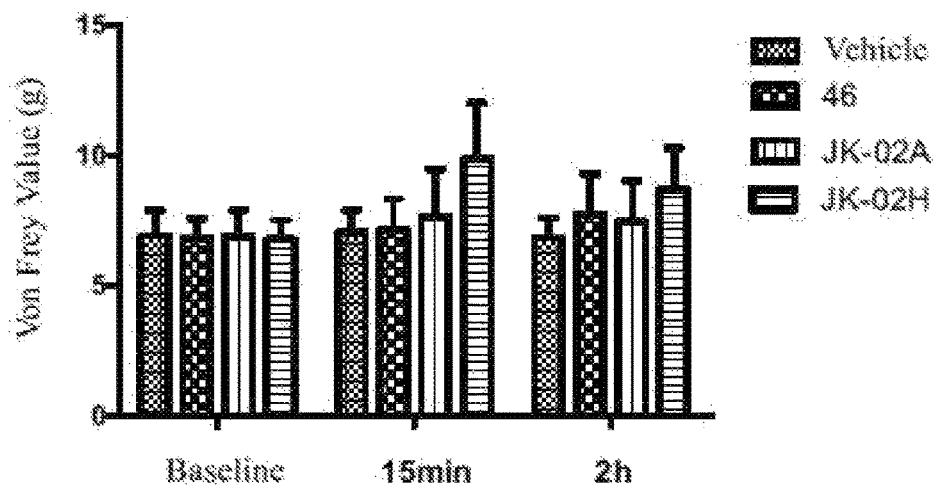

The group mean value of the Von Frey test with a low dose treatment is shown in Table 4 and FIGS. 1A-1B.

Figure 2A:
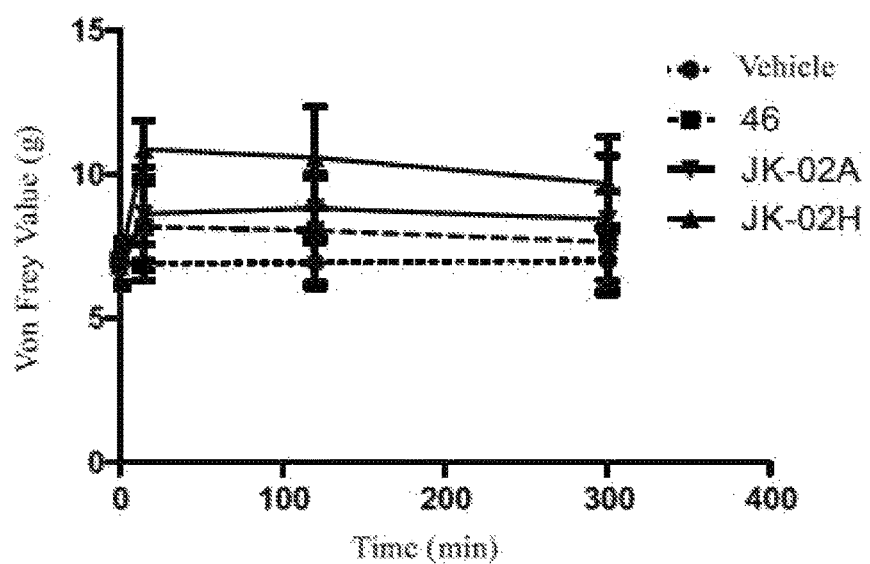
FIGS. 2A and 2B show the average value of each test compound in the Von Frey filament test under a high dose treatment.
Figure 2B:
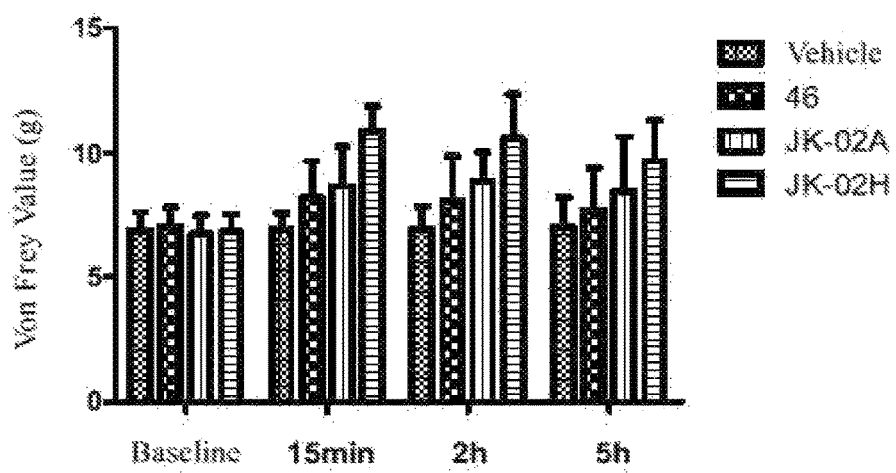

The group mean value of the Von Frey test with a high dose treatment is shown in Table 5 and FIGS. 2A-2B.

Figure 3:
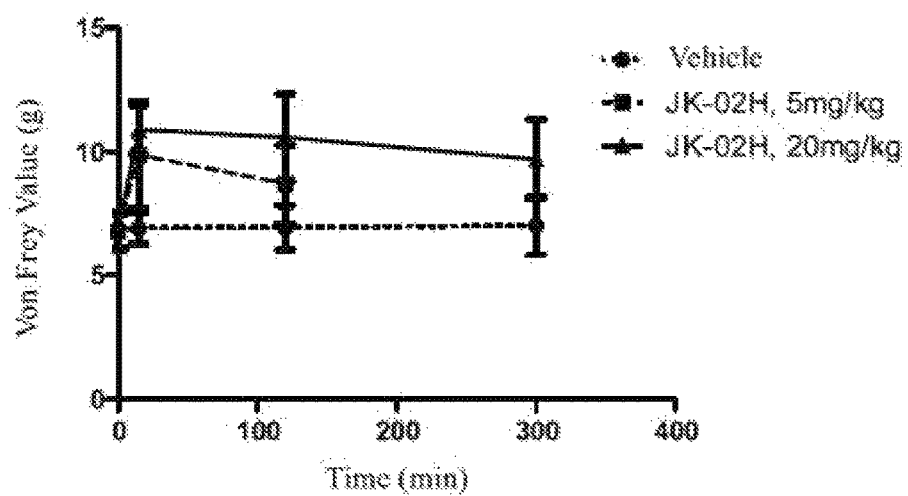
FIG. 3 shows the dose dependency of compound JK-02H in the Von Frey filament test.

The Von Frey filament test values of individual animal are summarized in Table 9. The dose dependency of JK-02H in the Von Frey filament test is shown in FIG. 3.

TABLE 4

Von Frey Filament Test Values of All the Groups with a Low Dose Treatment (Mean ± SD)

| Treatment | Dose (mg/kg) | Number | Baseline | 15 min | 2 h |
| --- | --- | --- | --- | --- | --- |
| CFA + Vehicle | — | 8 | 6.91 ± 0.95 | 7.02 ± 0.86 | 6.84 ± 0.75 |
| CFA + 46 | 10 | 8 | 6.81 ± 0.74 | 7.12 ± 1.20 | 7.69 ± 1.59 |
| CFA + JK-02A | 10 | 8 | 6.89 ± 0.99 | 7.64 ± 1.83 | 7.43 ± 1.62 |
| CFA + JK-02H | 5 | 8 | 6.76 ± 0.73 | 9.85 ± 2.15** | 8.69 ± 1.57** |

Notes:
* $p < 0.05$, compared with vehicle
** $p < 0.01$, compared with vehicle

TABLE 5

Von Frey Filament Test Values of All the Group with a High Dose Treatment (Mean ± SD)

| Treatment | Dose (mg/kg) | Number | Baseline | 15 min | 2 h | 5 h |
| --- | --- | --- | --- | --- | --- | --- |
| CFA + Vehicle | — | 8 | 6.86 ± 0.73 | 6.91 ± 0.63 | 6.93 ± 0.89 | 7.01 ± 1.18 |
| CFA + 46 | 40 | 8 | 7.01 ± 0.75 | 8.17 ± 1.50* | 8.04 ± 1.83 | 7.66 ± 1.72 |
| CFA + JK-02A | 40 | 8 | 6.73 ± 0.74 | 8.63 ± 1.62* | 8.82 ± 1.20* | 8.45 ± 2.18 |
| CFA + JK-02H | 20 | 8 | 6.81 ± 0.70 | 10.87 ± 1.00** | 10.57 ± 1.76** | 9.68 ± 1.63** |

Figure 4A:
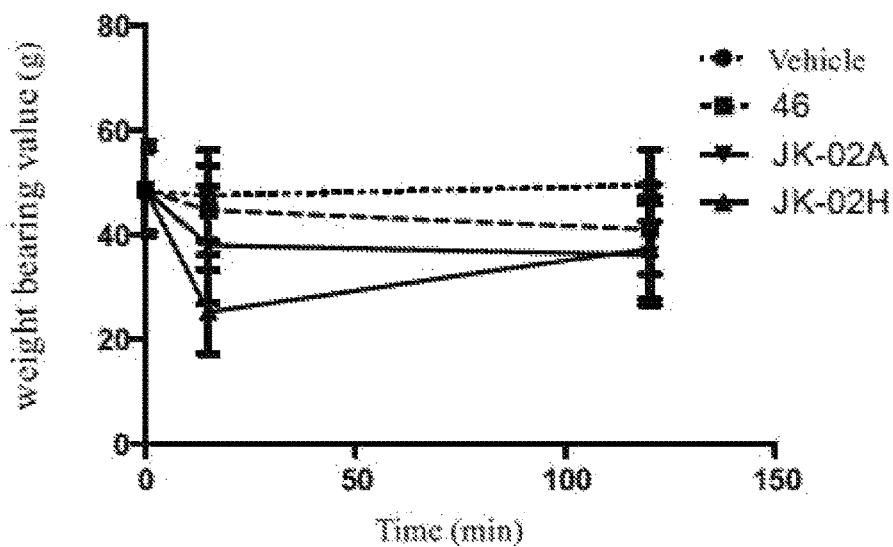
FIGS. 4A and 4B show the average value of each test compound in the weight bearing test under a low dose treatment.
Figure 4B:
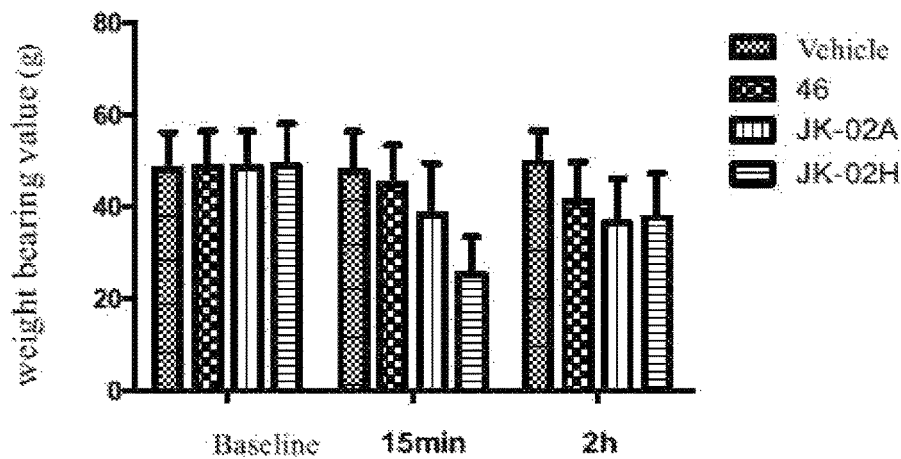

Notes:
*$p < 0.05$, compared with vehicle
$p < 0.01$, compared with vehicle 3.2 Weight Bearing Test The group mean value of the weight bearing test with a low dose treatment is shown in Table 6 and FIGS. 4A-4B**.

Figure 5A:
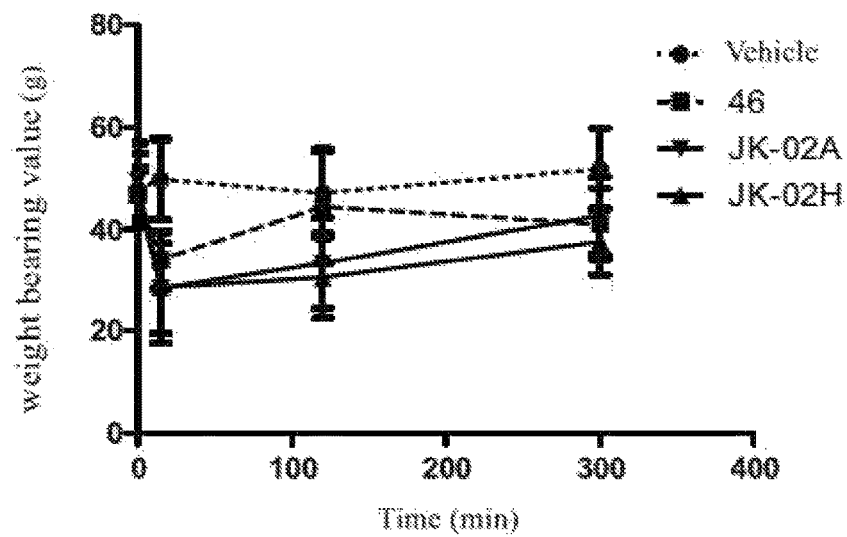
FIGS. 5A and 5B show the average value of each test compound in the weight bearing test under a high dose treatment.
Figure 5B:
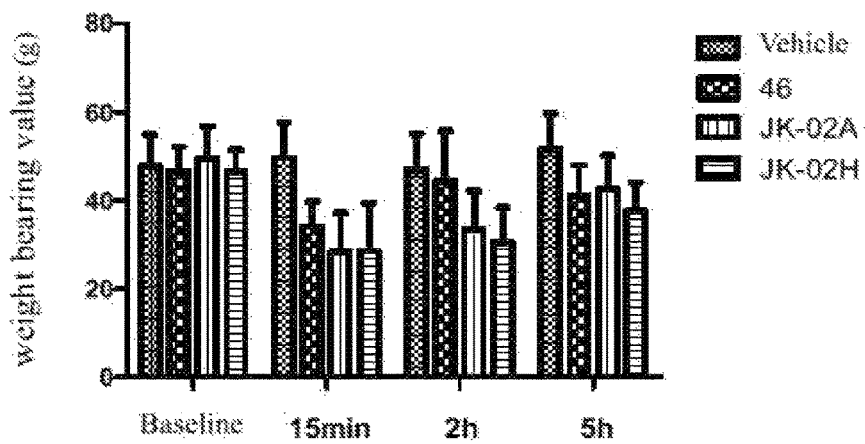

The group mean value of the weight bearing test with a high dose treatment is shown in Table 7 and FIGS. 5A-5B.

The weight bearing test values of individual animal are summarized in Table 10.

Figure 6:
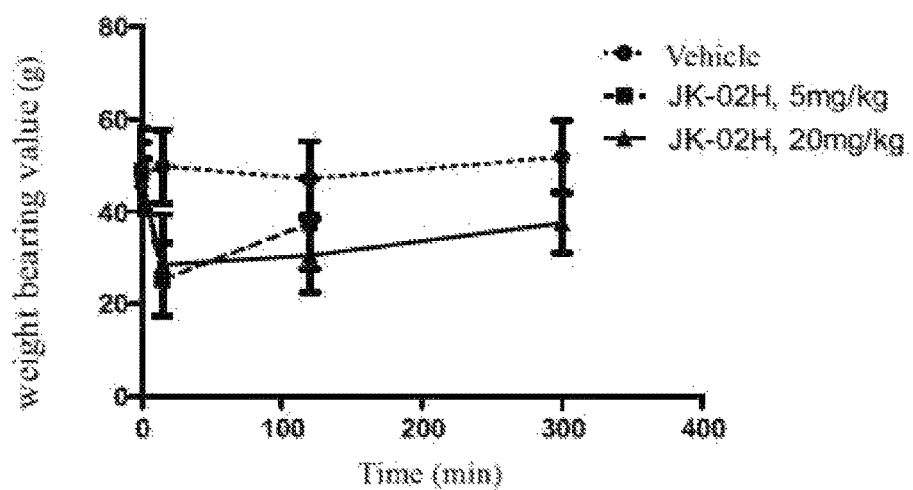
FIG. 6 shows the dose dependency of compound JK-02H in the weight bearing test.

The dose dependency of JK-02H in the weight-bearing test is shown in FIG. 6.

TABLE 6

Weight Bearing Test Values of All the Groups with a Low Dose Treatment (Mean ± SD)

| Treatment | Dose (mg/kg) | Number | Baseline | 15 min | 2 h |
| --- | --- | --- | --- | --- | --- |
| CFA + Vehicle | — | 8 | 48.25 ± 7.88 | 47.54 ± 8.68 | 49.48 ± 6.89 |
| CFA + 46 | 10 | 8 | 48.54 ± 7.73 | 44.76 ± 8.54 | 41.09 ± 8.58* |
| CFA + JK-02A | 10 | 8 | 48.18 ± 5.05 | 38.11 ± 11.23 | 36.24 ± 9.72** |
| CFA + JK-02H | 5 | 8 | 48.83 ± 9.15 | 25.30 ± 7.97** | 37.43 ± 9.77* |

Notes:
*$p < 0.05$, compared with vehicle
**$p < 0.01$, compared with vehicle

TABLE 7

Weight Bearing Test Values of All the Groups with a High Dose Treatment (Mean ± SD)

| Treatment | Dose (mg/kg) | Number | Baseline | 15 min | 2 h | 5 h |
|---|---|---|---|---|---|---|
| CFA + Vehicle | — | 8 | 47.69 ± 7.29 | 49.75 ± 7.92 | 47.13 ± 8.02 | 51.75 ± 8.00 |
| CFA + 46 | 40 | 8 | 46.73 ± 5.58 | 34.03 ± 5.67** | 44.46 ± 11.29 | 41.06 ± 6.98* |
| CFA + JK-02A | 40 | 8 | 49.54 ± 7.39 | 28.43 ± 8.83** | 33.36 ± 8.92** | 42.69 ± 7.52* |
| CFA + JK-02H | 20 | 8 | 46.68 ± 4.82 | 28.55 ± 10.91** | 30.48 ± 7.88** | 37.58 ± 6.58** |

Notes:
*$p < 0.05$, compared with vehicle
**$p < 0.01$, compared with vehicle

4. Conclusions

The effects of compounds 46, JK-02A and JK-02H on CFA induced hyperalgesia in rats were assessed with Von Frey and weight bearing tests following single injection. The results showed that compound JK-02H exhibited significant anti-hyperalgesia effects at both a high dose (20 mg/kg) and a low dose (5 mg/kg) compared with the vehicle group; while compounds 46 and JK-02A showed anti-hyperalgesia effects only at a high dose (40 mg/kg), and the anti-hyperalgesia effects thereof were not significant at a low dose (10 mg/kg). In addition, compound JK-02H at the high dose still exhibited a very remarkable therapeutic effect even when the test time was prolonged to 5 h, indicating compound JK-02H may have a relatively long half-life.

TABLE 8

Von Frey and Weight Bearing's Baselines of Individual Animal

| Group | ID | First Baseline | | | | Second Baseline | | | |
|---|---|---|---|---|---|---|---|---|---|
| | | | Balance | | | | Balance | | |
| | | Von Frey | Left | Right | Δ | Von Frey | Left | Right | Δ |
| Vehicle | 4 | 5.1 | 4.7 | 42.7 | 89.3 | 46.6 | 7.9 | 7.2 | 28.0 | 77.1 | 49.1 |
| | 47 | 6.7 | 5.7 | 36.6 | 81.8 | 45.2 | 5.5 | 5.5 | 36.0 | 96.1 | 60.1 |
| | 21 | 6.6 | 7.5 | 48.9 | 113.7 | 64.8 | 7.1 | 6.1 | 61.3 | 102.3 | 41.0 |
| | 33 | 7.3 | 7.3 | 33.4 | 73.4 | 40.0 | 8.3 | 7.0 | 37.4 | 77.4 | 40.0 |
| | 11 | 7.6 | 6.3 | 50.4 | 102.7 | 52.3 | 7.4 | 6.1 | 58.8 | 108.2 | 49.4 |
| | 45 | 7.5 | 7.3 | 48.8 | 89.3 | 40.5 | 7.1 | 7.6 | 52.8 | 96.5 | 43.7 |
| | 7 | 7.6 | 8.1 | 46.2 | 93.1 | 46.9 | 6.7 | 5.8 | 58.0 | 100.4 | 42.4 |
| | 3 | 7.7 | 7.5 | 50.0 | 99.7 | 49.7 | 6.7 | 7.7 | 54.0 | 109.8 | 55.8 |
| 46 | 20 | 7.4 | 5.4 | 31.3 | 83.6 | 52.3 | 7.6 | 7.7 | 61.3 | 115.3 | 54.0 |
| | 26 | 6.2 | 6.1 | 27.8 | 87.0 | 59.2 | 6.4 | 6.2 | 45.0 | 95.2 | 50.2 |
| | 30 | 6.4 | 6.1 | 41.8 | 91.8 | 50.0 | 5.5 | 5.7 | 70.0 | 119.5 | 49.5 |
| | 28 | 6.3 | 5.5 | 63.2 | 105.0 | 41.8 | 7.1 | 6.2 | 51.2 | 104.5 | 53.3 |
| | 48 | 7.5 | 7.0 | 73.9 | 114.0 | 40.1 | 7.9 | 7.0 | 34.7 | 76.6 | 41.9 |
| | 6 | 7.3 | 6.7 | 49.6 | 102.9 | 53.3 | 7.3 | 7.6 | 24.8 | 67.1 | 42.3 |
| | 37 | 7.6 | 7.6 | 33.9 | 71.5 | 37.6 | 7.2 | 8.1 | 43.5 | 84.3 | 40.8 |
| | 40 | 8.1 | 7.7 | 60.4 | 114.4 | 54.0 | 7.5 | 7.2 | 65.5 | 107.3 | 41.8 |
| JK-02A | 41 | 5.1 | 5.9 | 54.2 | 103.7 | 49.5 | 7.1 | 7.1 | 32.1 | 89.3 | 57.2 |
| | 25 | 5.8 | 6.5 | 57.2 | 98.1 | 40.9 | 5.3 | 5.2 | 47.3 | 90.0 | 42.7 |
| | 19 | 6.9 | 6.2 | 45.5 | 93.0 | 47.5 | 7.4 | 7.3 | 30.4 | 81.0 | 50.6 |
| | 35 | 5.2 | 6.8 | 64.4 | 117.4 | 53.0 | 6.0 | 7.6 | 45.9 | 87.2 | 41.3 |
| | 31 | 7.8 | 6.8 | 45.6 | 90.5 | 44.9 | 6.4 | 6.6 | 50.1 | 92.4 | 52.3 |
| | 12 | 7.3 | 7.6 | 12.0 | 66.3 | 54.3 | 7.7 | 7.5 | 39.6 | 90.4 | 50.8 |
| | 43 | 7.9 | 7.6 | 58.0 | 100.6 | 42.6 | 5.8 | 6.7 | 33.5 | 94.1 | 60.6 |
| | 22 | 8.2 | 8.6 | 64.0 | 116.7 | 52.7 | 7.5 | 6.4 | 57.1 | 97.9 | 40.8 |
| JK-02H | 10 | 4.9 | 5.8 | 62.6 | 96.2 | 33.6 | 5.2 | 5.4 | 43.2 | 86.1 | 42.9 |
| | 14 | 5.8 | 6.7 | 45.6 | 96.2 | 50.6 | 8.4 | 6.7 | 65.0 | 110.8 | 45.8 |
| | 42 | 7.7 | 6.1 | 51.0 | 101.1 | 50.1 | 6.6 | 6.4 | 68.9 | 113.2 | 44.3 |
| | 39 | 7.0 | 7.1 | 60.6 | 115.5 | 54.9 | 7.3 | 7.1 | 61.3 | 115.1 | 53.8 |
| | 1 | 6.4 | 7.4 | 48.8 | 89.7 | 40.9 | 6.8 | 7.6 | 47.2 | 93.6 | 46.4 |
| | 36 | 7.4 | 7.3 | 56.5 | 121.0 | 64.5 | 7.4 | 6.6 | 60.6 | 102.8 | 42.2 |
| | 38 | 8.0 | 7.5 | 38.6 | 87.7 | 49.1 | 6.9 | 6.2 | 50.2 | 93.7 | 43.5 |
| | 17 | 5.8 | 7.3 | 64.0 | 110.9 | 46.9 | 7.3 | 7.0 | 51.8 | 106.3 | 54.5 |

TABLE 9

Von Frey Values of Individual Animal

| Group | ID | Day 7 15 min | | 2 h | | Day 14 15 min | | 2 h | | 5 h | |
|---|---|---|---|---|---|---|---|---|---|---|---|
| Vehicle | 4 | 6.7 | 7.7 | 6.2 | 5.9 | 6.7 | 8.2 | 6.3 | 6.1 | 6.5 | 5.9 |
|  | 47 | 5.0 | 5.6 | 6.0 | 5.2 | 5.1 | 6.1 | 6.7 | 7.0 | 8.9 | 8.0 |
|  | 21 | 6.7 | 6.7 | 7.3 | 7.0 | 6.6 | 6.6 | 7.7 | 7.4 | 6.7 | 7.5 |
|  | 33 | 8.5 | 8.0 | 7.9 | 7.7 | 6.1 | 7.8 | 7.1 | 7.9 | 7.8 | 6.0 |
|  | 11 | 7.6 | 7.0 | 7.4 | 6.6 | 7.1 | 6.7 | 8.5 | 7.2 | 7.6 | 8.7 |
|  | 45 | 7.8 | 7.0 | 6.4 | 6.6 | 8.2 | 6.5 | 5.0 | 6.6 | 5.1 | 5.1 |
|  | 7 | 7.0 | 7.8 | 7.9 | 6.1 | 7.6 | 7.6 | 7.3 | 8.5 | 7.9 | 8.3 |
|  | 3 | 6.6 | 6.6 | 7.4 | 7.8 | 7.0 | 6.7 | 6.5 | 5.1 | 6.4 | 5.8 |
| 46 | 20 | 7.6 | 7.5 | 9.3 | 8.8 | 7.3 | 9.0 | 5.8 | 7.3 | 6.6 | 7.5 |
|  | 26 | 6.8 | 7.6 | 9.4 | 8.6 | 8.3 | 7.5 | 8.2 | 7.0 | 7.1 | 6.1 |
|  | 30 | 6.6 | 5.5 | 6.5 | 5.8 | 9.6 | 10.8 | 6.2 | 7.1 | 5.9 | 6.3 |
|  | 28 | 8.2 | 7.5 | 5.9 | 6.5 | 7.0 | 6.7 | 8.9 | 7.2 | 8.8 | 7.5 |
|  | 48 | 5.9 | 7.9 | 7.4 | 6.5 | 9.6 | 8.2 | 5.9 | 5.9 | 6.8 | 5.8 |
|  | 6 | 4.6 | 5.3 | 5.5 | 5.9 | 5.5 | 5.6 | 8.9 | 8.5 | 6.6 | 7.0 |
|  | 37 | 9.0 | 8.9 | 8.4 | 9.3 | 8.2 | 8.0 | 9.7 | 8.8 | 8.7 | 9.9 |
|  | 40 | 7.8 | 7.2 | 9.4 | 9.8 | 10.5 | 8.9 | 11.1 | 12.1 | 11.7 | 10.3 |
| JK-02A | 41 | 9.1 | 8.8 | 6.6 | 5.6 | 9.3 | 8.9 | 8.7 | 9.8 | 11.9 | 13.2 |
|  | 25 | 6.3 | 5.6 | 7.0 | 8.3 | 6.5 | 7.4 | 8.7 | 9.5 | 6.7 | 5.2 |
|  | 19 | 10.2 | 8.9 | 7.4 | 6.0 | 10.9 | 9.5 | 9.3 | 9.4 | 8.3 | 9.2 |
|  | 35 | 10.0 | 9.5 | 7.0 | 8.9 | 7.4 | 6.1 | 9.1 | 8.5 | 9.7 | 9.8 |
|  | 31 | 9.1 | 9.5 | 10.5 | 10.4 | 12.5 | 10.6 | 9.2 | 8.2 | 8.8 | 9.9 |
|  | 12 | 5.7 | 5.6 | 6.5 | 7.0 | 9.5 | 7.6 | 8.9 | 9.6 | 6.4 | 5.7 |
|  | 43 | 7.3 | 6.0 | 7.1 | 7.3 | 9.2 | 8.5 | 10.6 | 9.3 | 7.3 | 8.9 |
|  | 22 | 9.4 | 9.1 | 5.1 | 4.9 | 10.7 | 9.1 | 6.2 | 5.8 | 7.4 | 6.8 |
| JK-02H | 10 | 6.5 | 5.5 | 7.0 | 6.2 | 11.6 | 11.4 | 7.1 | 8.9 | 7.3 | 8.9 |
|  | 14 | 11.9 | 13.8 | 11.4 | 11.2 | 9.4 | 10.9 | 11.3 | 10.8 | 8.7 | 9.5 |
|  | 42 | 8.6 | 8.5 | 8.7 | 9.0 | 9.7 | 10.3 | 9.2 | 7.2 | 8.7 | 7.1 |
|  | 39 | 10.5 | 11.3 | 7.5 | 6.5 | 9.4 | 10.1 | 12.0 | 10.8 | 7.4 | 8.5 |
|  | 1 | 8.7 | 8.5 | 8.5 | 10.8 | 11.4 | 11.1 | 9.8 | 10.5 | 11.0 | 9.8 |
|  | 36 | 9.3 | 9.7 | 10.8 | 8.4 | 10.8 | 10.4 | 10.3 | 11.4 | 11.3 | 9.9 |
|  | 38 | 11.4 | 10.5 | 8.7 | 9.4 | 12.0 | 13.7 | 11.0 | 12.3 | 11.2 | 12.6 |
|  | 17 | 11.3 | 11.7 | 7.5 | 7.5 | 11.7 | 10.0 | 13.0 | 13.5 | 12.1 | 10.9 |

TABLE 10

Weight Bearing Values of Individual Animal

| Group | ID | Day 7 15 min | | | 2 h | | | Day 14 15 min | | | 2 h | | | 5 h | | |
|---|---|---|---|---|---|---|---|---|---|---|---|---|---|---|---|---|
|  |  | Left | Right | Δ | Left | Right | Δ | Left | Right | Δ | Left | Right | Δ | Left | Right | Δ |
| Vehicle | 4 | 41.4 | 84.3 | 42.9 | 40.8 | 88.2 | 47.4 | 25.9 | 73.1 | 47.2 | 21.0 | 76.2 | 55.2 | 39.0 | 99.8 | 60.8 |
|  | 47 | 30.6 | 73.2 | 42.6 | 35.3 | 78.7 | 43.4 | 39.6 | 90.1 | 50.5 | 33.9 | 85.2 | 51.3 | 45.9 | 94.1 | 48.2 |
|  | 21 | 39.3 | 96.9 | 57.6 | 45.9 | 88.6 | 42.7 | 64.1 | 99.8 | 35.7 | 63.5 | 97.8 | 34.3 | 63.9 | 118.0 | 54.1 |
|  | 33 | 30.4 | 92.3 | 61.9 | 47.0 | 103.8 | 56.8 | 55.9 | 108.9 | 53.0 | 58.6 | 103.9 | 45.3 | 56.6 | 91.5 | 34.9 |
|  | 11 | 50.0 | 98.8 | 48.8 | 45.8 | 103.3 | 57.5 | 72.7 | 117.4 | 44.7 | 69.8 | 116.2 | 46.4 | 40.6 | 98.0 | 57.4 |
|  | 45 | 30.1 | 76.3 | 46.2 | 41.8 | 83.0 | 41.2 | 53.3 | 108.1 | 54.8 | 50.9 | 110.5 | 59.6 | 54.4 | 107.5 | 53.1 |
|  | 7 | 50.1 | 95.8 | 45.7 | 42.3 | 99.4 | 57.1 | 49.9 | 112.8 | 62.9 | 51.1 | 93.1 | 42.0 | 59.6 | 108.6 | 49.0 |
|  | 3 | 43.0 | 77.6 | 34.6 | 57.8 | 107.5 | 49.7 | 41.5 | 90.7 | 49.2 | 48.1 | 91.0 | 42.9 | 51.5 | 108.0 | 56.5 |
| 46 | 20 | 47.4 | 93.5 | 46.1 | 48.5 | 91.5 | 43.0 | 62.4 | 96.4 | 34.0 | 59.9 | 107.1 | 47.2 | 55.9 | 102.4 | 46.5 |
|  | 26 | 40.2 | 94.1 | 53.9 | 39.0 | 81.8 | 42.8 | 64.0 | 104.7 | 40.7 | 68.1 | 101.0 | 32.9 | 34.5 | 85.3 | 50.8 |
|  | 30 | 67.4 | 110.9 | 43.5 | 65.0 | 102.9 | 37.9 | 61.5 | 95.1 | 33.6 | 65.7 | 112.2 | 46.5 | 56.8 | 101.8 | 45.0 |
|  | 28 | 60.4 | 89.1 | 28.7 | 66.3 | 97.7 | 31.4 | 63.7 | 95.7 | 32.0 | 44.8 | 110.9 | 66.1 | 58.2 | 88.4 | 30.2 |
|  | 48 | 40.3 | 91.2 | 50.9 | 48.4 | 80.7 | 32.3 | 59.2 | 96.9 | 37.7 | 56.2 | 98.5 | 42.3 | 47.3 | 90.0 | 42.7 |
|  | 6 | 39.0 | 81.7 | 42.7 | 43.4 | 82.3 | 38.9 | 39.7 | 71.9 | 32.2 | 36.9 | 87.3 | 50.4 | 31.3 | 66.5 | 35.2 |
|  | 37 | 24.3 | 62.7 | 38.4 | 38.0 | 81.5 | 43.5 | 52.6 | 75.2 | 22.6 | 65.4 | 94.8 | 29.4 | 41.6 | 76.3 | 34.7 |
|  | 40 | 58.1 | 112.0 | 53.9 | 54.8 | 113.7 | 58.9 | 68.4 | 107.8 | 39.4 | 67.0 | 107.9 | 40.9 | 73.0 | 116.4 | 43.4 |
| JK-02A | 41 | 36.6 | 83.8 | 47.2 | 68.5 | 99.4 | 30.9 | 58.9 | 77.1 | 18.2 | 66.8 | 97.0 | 30.2 | 38.0 | 77.2 | 39.2 |
|  | 25 | 56.4 | 79.1 | 22.7 | 68.0 | 85.5 | 17.5 | 57.8 | 95.3 | 37.5 | 71.9 | 106.5 | 34.6 | 62.9 | 99.3 | 36.4 |
|  | 19 | 47.8 | 74.1 | 26.3 | 31.5 | 80.7 | 49.2 | 49.6 | 77.6 | 28.0 | 48.9 | 97.2 | 48.3 | 55.0 | 93.8 | 38.8 |
|  | 35 | 37.9 | 89.5 | 51.6 | 39.9 | 75.7 | 35.8 | 53.7 | 90.1 | 36.4 | 60.7 | 81.1 | 20.4 | 45.7 | 90.7 | 45.0 |
|  | 31 | 36.9 | 62.9 | 26.0 | 43.9 | 77.3 | 33.4 | 52.7 | 80.4 | 27.7 | 50.1 | 79.8 | 29.7 | 52.7 | 92.0 | 39.3 |
|  | 12 | 50.5 | 93.7 | 43.2 | 37.3 | 73.4 | 36.1 | 50.9 | 80.1 | 29.2 | 54.6 | 91.1 | 36.5 | 39.7 | 99.9 | 60.2 |
|  | 43 | 25.4 | 69.1 | 43.7 | 52.3 | 95.8 | 43.5 | 67.1 | 104.0 | 36.9 | 44.8 | 86.5 | 41.7 | 54.9 | 95.3 | 40.4 |
|  | 22 | 65.6 | 109.8 | 44.2 | 62.2 | 105.7 | 43.5 | 72.2 | 85.7 | 13.5 | 72.2 | 97.7 | 25.5 | 68.2 | 110.4 | 42.2 |
| JK-02H | 10 | 54.2 | 77.2 | 23.0 | 42.3 | 66.8 | 24.5 | 59.4 | 82.5 | 23.1 | 75.2 | 95.7 | 20.5 | 63.5 | 94.2 | 30.7 |
|  | 14 | 73.4 | 99.2 | 25.8 | 29.7 | 74.0 | 44.3 | 69.4 | 90.8 | 21.4 | 69.4 | 104.8 | 35.4 | 62.4 | 111.2 | 48.8 |
|  | 42 | 30.9 | 71.7 | 40.8 | 57.5 | 106.2 | 48.7 | 72.7 | 92.9 | 20.2 | 47.2 | 90.0 | 42.8 | 66.3 | 105.6 | 39.3 |
|  | 39 | 63.3 | 77.8 | 14.5 | 72.9 | 97.7 | 24.8 | 72.8 | 99.1 | 26.3 | 71.7 | 96.8 | 25.1 | 54.9 | 95.6 | 40.7 |

TABLE 10-continued

Weight Bearing Values of Individual Animal

| Group | ID | Day 7 | | | | | | Day 14 | | | | | | | | |
|---|---|---|---|---|---|---|---|---|---|---|---|---|---|---|---|---|
| | | 15 min | | | 2 h | | | 15 min | | | 2 h | | | 5 h | | |
| | | Left | Right | Δ | Left | Right | Δ | Left | Right | Δ | Left | Right | Δ | Left | Right | Δ |
| | 1 | 46.3 | 72.4 | 26.1 | 23.1 | 71.6 | 48.5 | 23.1 | 77.6 | 54.5 | 76.8 | 99.9 | 23.1 | 63.8 | 95.1 | 31.3 |
| | 36 | 67.8 | 85.5 | 17.7 | 37.3 | 77.0 | 39.7 | 55.7 | 82.3 | 26.6 | 55.9 | 93.7 | 37.8 | 57.7 | 88.7 | 31.0 |
| | 38 | 45.1 | 75.2 | 30.1 | 43.5 | 81.2 | 37.7 | 42.0 | 70.4 | 28.4 | 47.9 | 80.6 | 32.7 | 47.6 | 83.3 | 35.7 |
| | 17 | 60.6 | 85.0 | 24.4 | 51.9 | 83.1 | 31.2 | 55.0 | 82.9 | 27.9 | 71.7 | 98.1 | 26.4 | 44.0 | 87.1 | 43.1 |

What is claimed is:

1. A method for treating pain, comprising administering to a subject in need thereof a therapeutically effective amount of a compound of Formula I or a pharmaceutically acceptable salt thereof, or a pharmaceutical composition comprising the compound of Formula I or the pharmaceutically acceptable salt thereof,

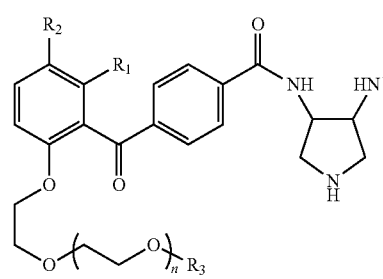

I wherein $R_1$ and $R_2$ are the same or different, each independently selected from the group consisting of halogen, $C_1$-$C_6$ alkoxyl, $C_1$-$C_6$ alkyl, $C_2$-$C_6$ alkenyl and $C_2$-$C_6$ alkynyl;
$R_3$ is selected from the group consisting of H, halogen, substituted or unsubstituted $C_1$-$C_6$ alkyl, $C_2$-$C_6$ alkenyl, $C_2$-$C_6$ alkynyl; and
n is an integer from 0 to 15.

2. The method according to claim 1, wherein $R_1$ and $R_2$ are each independently selected from the group consisting of halogen and $C_1$-$C_6$ alkoxyl.

3. The method according to claim 1, wherein $R_1$ is F, and $R_2$ is F or $OCH_3$.

4. The method according to claim 1, wherein the compound has the structure of Formula II:

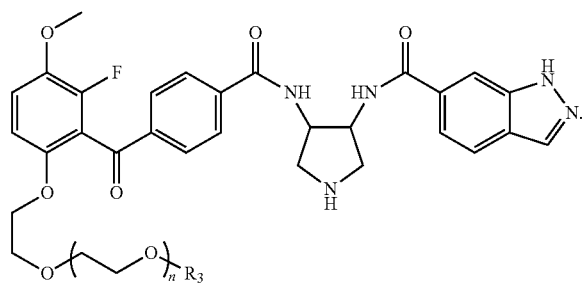

II

5. The method according to claim 1, wherein the compound has the structure of Formula III:

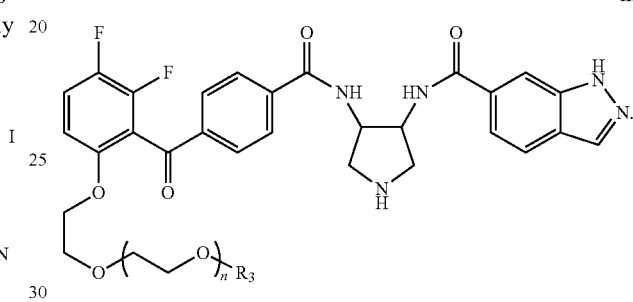

III

6. The method according to claim 1, wherein $R_3$ is selected from the group consisting of H, and substituted or unsubstituted $C_1$-$C_6$ alkyl.

7. The method according to claim 1, wherein $R_3$ is selected from the group consisting of H, and substituted or unsubstituted $C_1$-$C_3$ alkyl.

8. The method according to claim 1, wherein $R_3$ is H, methyl or propyl.

9. The method according to claim 1, wherein n is an integer from 1 to 10.

10. The method according to claim 1, wherein n is an integer from 1 to 6.

11. The method according to claim 1, wherein the compound is selected from the group consisting of:

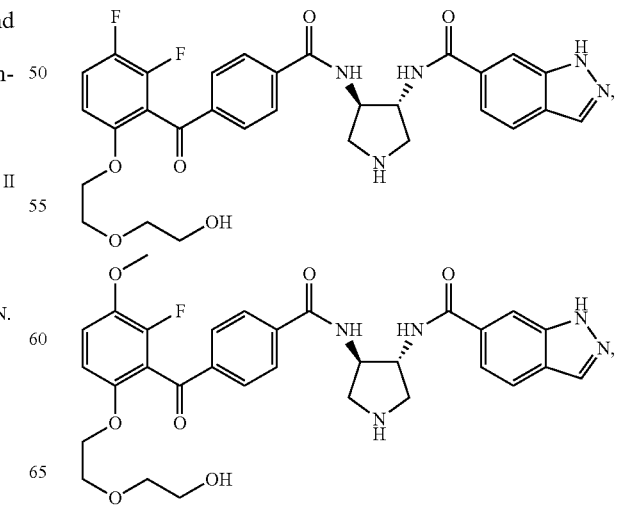

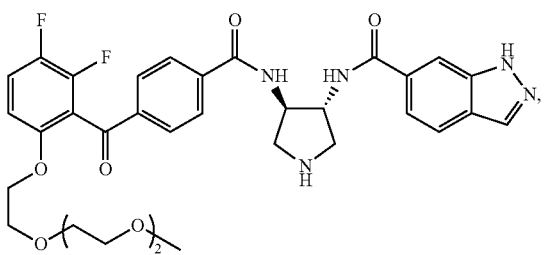
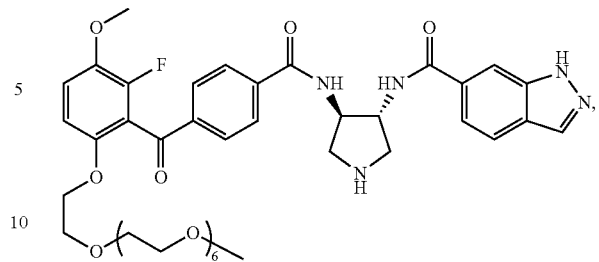
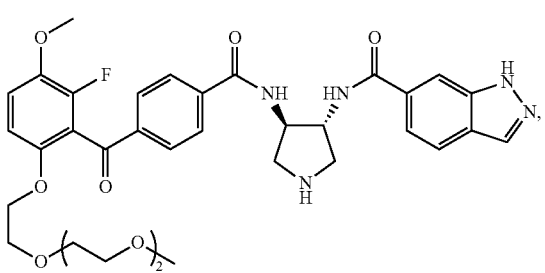
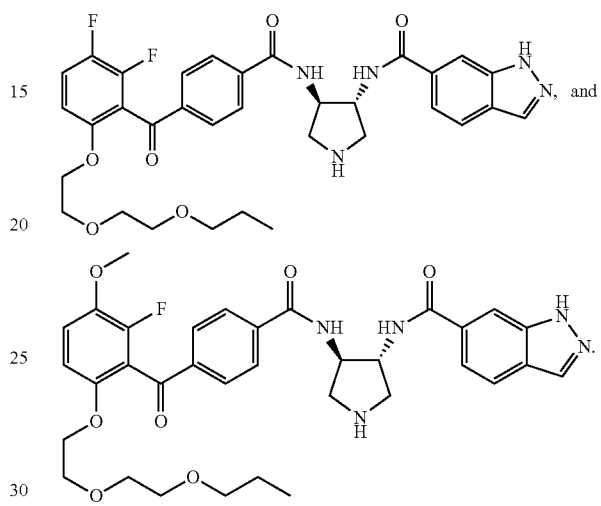
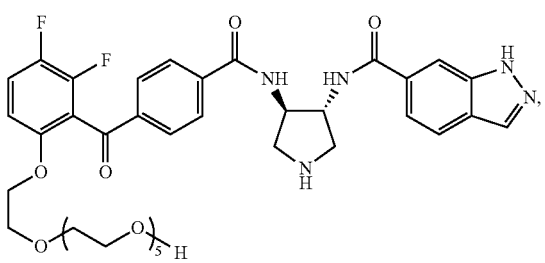
12. The method according to claim 1, wherein the compound is selected from the group consisting of:
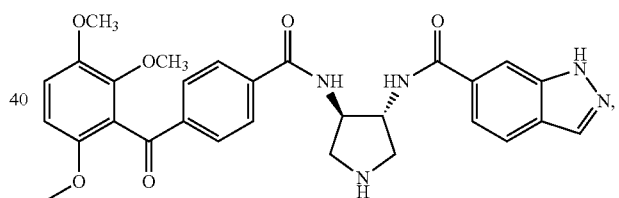
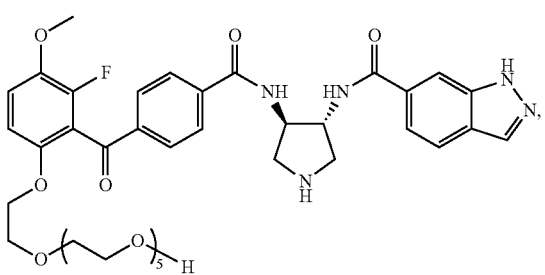
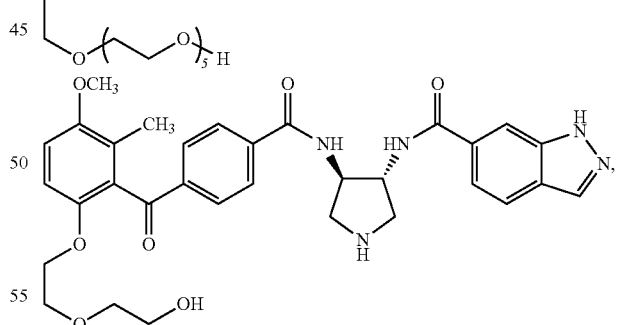
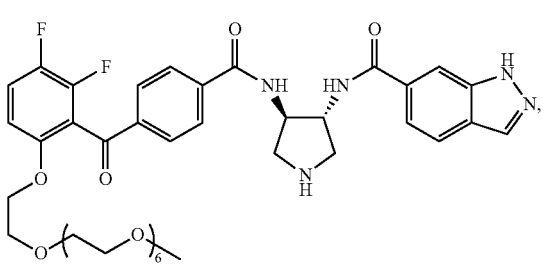
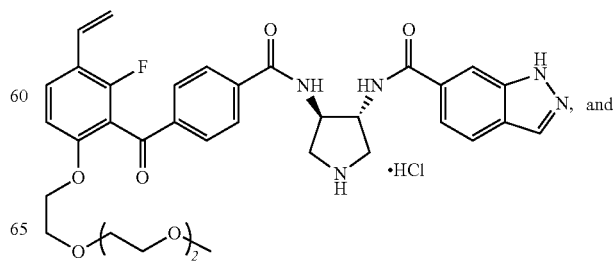

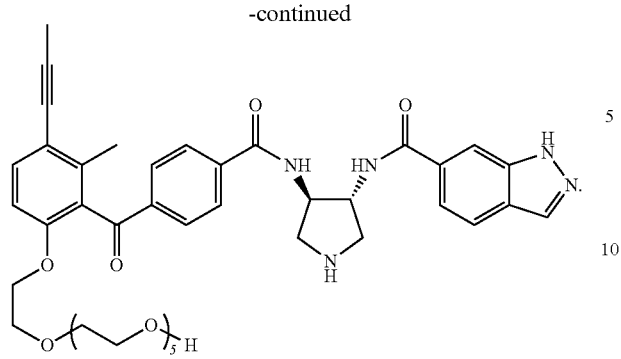
13. The method according to claim 1, wherein the pharmaceutically acceptable salt is selected from the group consisting of hydrochloride, sulfate, tartrate and citrate.
* * * * *